(12) United States Patent
Manoharan et al.

(10) Patent No.: US 6,486,313 B1
(45) Date of Patent: Nov. 26, 2002

(54) OLIGONUCLEOTIDES HAVING ALKYLPHOSPHONATE LINKAGES AND METHODS FOR THEIR PREPARATION

(75) Inventors: Muthiah Manoharan, Carlsbad, CA (US); George Just, Ile Cadieux (CA); Andrei Guzaev, Carlsbad, CA (US); Arlène Roland, Verdun (CA); Jianchao Wang, Montreal (CA); Michael E. Jung, Los Angeles, CA (US)

(73) Assignees: ISIS Pharmaceuticals, Inc., Carlsbad, CA (US); McGill University (CA)

( * ) Notice: Subject to any disclaimer, the term of this patent is extended or adjusted under 35 U.S.C. 154(b) by 0 days.

(21) Appl. No.: 09/252,521

(22) Filed: Feb. 18, 1999

(51) Int. Cl.$^7$ .................... C07H 21/02; C07H 21/04; C07H 21/00
(52) U.S. Cl. ............... 536/25.33; 536/25.3; 536/25.34; 536/25.6
(58) Field of Search ............... 536/25.33, 25.6, 536/25.3, 25.34

(56) References Cited

U.S. PATENT DOCUMENTS

| | | | |
|---|---|---|---|
| 3,687,808 A | 8/1972 | Merigan et al. | 195/28 |
| 5,210,264 A | 5/1993 | Yau | 558/167 |
| 5,670,633 A | 9/1997 | Cook et al. | 536/23.1 |

FOREIGN PATENT DOCUMENTS

| | | |
|---|---|---|
| WO | WO 94/00472 | 1/1994 |
| WO | WO 94/00473 | 1/1994 |

OTHER PUBLICATIONS

Jin et al., Tetrahedron Letters, vol. 39, pp. 6433–6436. 1998.*

JP 62–70391 A (Noroyi et al.) Mar. 31, 1987, col. 1–6 (abstract only).

Just et al. A Stereoselective Synthesis of Dinucleotide Boranophosphate, Using Chiral Indole–oxazaphosphorine Intermediates. Tetrahedron Letters. Jun. 1998, vol. 39, pp. 6433–6436. See entire document.

Guzaev et al. A Novel support for Synthesis of 3'–Phosphorylated Chimeric Oligonucleotides Containing Internucleosidic Methyl Phosphotriester and Methylphosphonate Linkages. Tetrahedron Letters, 1997, vol. 38, No. 22, pp. 3989–3992, see entire document.

Just et al. The Synthesis of the Sp and Rp Diastereomers of Dithymidine Boranophosphate Tetradedron Letters. May 1998, vol. 39, pp. 6429–6432, see entire document.

Agrawal et al. (eds.), "Methods of Molecular Biology", in *Protocols for Oligonucleotide Conjugates*, Agrawal, S. (ed.), Humana Press, New Jersey, 1994, vol. 26, 1–72.

Beaucage, S.L. et al., "Advances in the Synthesis of Oligonucleotides by the Phosphoramidite Approach", *Tetrahedron*, 1992, 48, 2223–2311.

Cook. P.D., "Medicinal Chemistry of Antisense Oligonucleotides—future opportunities", *Anti–Cancer Drug Design*, 1991, 6, 585–607.

Delgado, C. et al., "The Uses and Properties of PEG–Linked Proteins", *Crit. Rev. in Therapeutic Drug Carrier Sys.*, 1992, 9, 249–304.

Eisenhardt et al., "Backbone Modified Antisense Oligodeoxy–Nucleotides Directed Against the Hepatitis–C–Virus (HCV)–RNA", *Nucleosides & Nucleotides*, 1997, 16(7–9), 1669–1672.

Englisch, U. et al., "Chemically Modified Oligonucleotides as Probes and Inhibitors", *Angew. Chem. Int. Ed. Eng.*, 1991, 30, 613–629.

Hamm et al., Incorporation of 2'–Deoxy–2'–mercaptocytidine into Oligonucleotides via Phosphoramidite Chemistry, *J. Org. Chem.*, 1997, 62, 3415–3420.

Jaworska–Maslanka et al., "Studies on Stereospecific Formation of P–Chiral Internucleotide Linkage: Synthesis of all–Rp and all–Sp Methylphosphonate Pentanucleotide d(MMTrA$_{PMe}$T$_{PMe}$C$_{PMe}$TAc) via Grignard Activated Coupling", *Antisense & Nucl. Acid Drug Devel.*, 1997, 7, 23–30.

Kroschwitz, J.I., "Polynucleotides", *Concise Encyclopedia of Polymer Science and Engineering*, 1990, John Wiley & Sons, New York, 858–859.

Larock, R.C., *Comprehensive Organic Tranformations: A Guide To Functional Group Preparations*, VCH, New York, 1989, 411–415.

Miller et al., "Anticode Oligonucleoside Methylphosphonates and Their Psoralen Derivatives", *Antisense Research and Applications*, Crooke, S.T. et al. (eds.), CRC Press, Boca Raton, 1993, Ch. 10, 189–203.

Ouchi, T. et al., "Synthesis and Antitumor Activity of Poly(Ethylene Glycol)s Linked to 5'–Fluorouracil via a Urethane or Urea Bond", *Drug Des. & Disc.*, 1992, 9, 93–105.

Polushin et al., "Synthesis of Oligonucleotides Containing 2'–Azido– and 2'–Amino–2'–deoxyuridine Using Phosphotriester Chemistry", *Tetrahedron Lett.*, 1996, 37(19), 3227–3230.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.*, 1991, 56, 4329–4333.

(List continued on next page.)

Primary Examiner—James O. Wilson
Assistant Examiner—Howard V. Owens
(74) *Attorney, Agent, or Firm*—Woodcock Washburn LLP (57) ABSTRACT

The present invention provides alkylphosphonate dimers and oligonucleotides prepared therefrom. The invention further provides novel methods for the preparation of these alkylphosphonate dimers. Methods for the preparation of substantially diastereomerically pure alkylphosphonate dimers are also provided.

16 Claims, 4 Drawing Sheets

OTHER PUBLICATIONS

Seela, F. et al., "Diastereomerically Pure $R_P$ and $S_P$ Dinucleoside H–Phosphonates: The Stereochemical Course of Their Conversion into P–Methylphosphonates, Phosphorothioates, and [$^{18}$O] Chiral Phosphates", *J. Org. Chem.*, 1991, 56, 3861–3869.

Thomson, J. et al., "Synthesis and Properties of Diuridine Phosphate Analogues Containing Thio and Amino Modifications", *J. Org. Chem.*, 1996, 61, 6273–6281.

Wang, J.C. et al., "A Stereoselective Synthesis of Dinucleotide Phosphorothioates, Using Chiral Indol–oxazaphosphorine Intermediates", *Tetrahedron Lett.*, 1997, 38(22), 3797–3800.

U.S. patent application Ser. No. 08/398,901, Cook et al., filed Mar. 6, 1995.

U.S. patent application Ser. No. 09/123,108, Manoharan et al., Jul. 27, 1998.

U.S. patent application Ser. No. 09/130,973, Manoharan et al., Aug. 7, 1998.

* cited by examiner

OLIGONUCLEOTIDES HAVING ALKYLPHOSPHONATE LINKAGES AND METHODS FOR THEIR PREPARATION

FIELD OF THE INVENTION

The present invention relates to novel methods for the preparation of alkylphosphonate nucleoside dimers, oligomeric compounds and methods of using such oligomeric compounds. In accordance with preferred embodiments of the invention, the present methods provide for the preparation of substantially diastereomerically pure (or enriched) alkylphosphonate compounds from substantially diastereomerically pure (or enriched) starting materials.

BACKGROUND OF THE INVENTION

Modified oligonucleotides are of great value in molecular biological research and in applications such as anti-viral therapy. Modified oligonucleotides which can block RNA translation, and are nuclease resistant, are useful as antisense reagents. One such modification is the alkylphosphonate internucleotide linkage.

There are a number of properties associated with oligonucleotides having alkylphosphonate internucleoside linkages that are superior to native phosphodiester internucleotide linkages. The majority of research in this area has been with methylphosphonates (Miller et al., *Antisense Research and Applications*, 1993, pp. 189–203, Crooke, S. T. and Lebleu, B. (eds) CRC Press, Boca Raton). Oligonucleotides having methylphosphonate internucleotide linkages are isosteric to natural phosphate groups, have non-ionic backbones, are resistant to nucleases, have weak interactions with plasma proteins and can enter cells by passive diffusion or through absorptive endocytosis. Oligonucleotides having methylphosphonate internucleotide linkages are not substrates for RNase H when duplexed with RNA. When a chimeric oligonucleotide is prepared having a 2'-deoxy region flanked on either side by methylphosphonate regions, the resulting oligonucleotide is able to withstand intracellular nuclease degradation until bound to a target RNA. Upon formation of an oligonucleotide/target RNA duplex the 2'-deoxy region becomes a substrate for RNase H and thus can give rise to a terminating event.

In addition to chemical modifications of the internucleoside linkage, the chirality of each phosphorus containing internucleoside linkage also effects the ability of a modified oligonucleotide to bind to RNA. The standard oxidation of a phosphite to a phosphate internucleotide linkages results in attack on either side of the phosphorous atom resulting in Rp and Sp diastereomers. Modified phosphorus oligonucleotides are racemic mixtures having $2^n$ isomers, with n equal to the number of intersugar linkages in the oligonucleotide. Thus, a 15-mer modified oligonucleotide, containing 14 asymmetric centers has $2^{14}$ or 16,384 diastereomers. In view of this, in a racemic mixture, only a small percentage of the oligonucleotides are likely to specifically hybridize to a target mRNA or DNA with optimal affinity.

Backbone chirality may also affect the susceptibility of an oligonucleotide-RNA heteroduplex to RNase H activity. The ability to serve as a template for RNase H has significant therapeutic implications since it has been suggested that RNase H causes cleavage of the RNA component in an RNA-DNA oligonucleotide heteroduplex. For a variety of catalytic reactions, hydrolysis of the phosphodiester backbone of nucleic acids proceeds by a stereospecific mechanism (an in-line mechanism) and inversion of configuration. Therefore, there may be only a small percentage of oligonucleotides in a racemic mixture that contain the correct chirality for maximum hybridization efficiency and termination of translation. Thus, increasing the percentage of internucleotide linkages that are diastereomerically enriched that can serve as substrates for RNase H in a heteroduplex will likely lead to a more efficacious compound for antisense and other oligonucleotide therapies.

Oligonucleotides having pure Rp or Sp methylphosphonate internucleotide linkages have been prepared by a number of routes. The separation of a mixture of H-phosphonate diastereomers into pure Rp and Sp stereoisomers followed by alkylation with retention of configuration has given the corresponding pure Sp or Rp methylphosphonate (Seela, F., Kretschmer, U., *J. Org. Chem.*, 1991, 56, 3861–3869). Another method requires the separation of a mixture of Rp and Sp 5'-O-protected-2'-O-deoxynucleosyl-3'-O-methylphosphinate (International Patent Application PCT/US93/06251, entitled "Trivalent Synthesis of Oligonucleotides Containing Stereospecific Alkylphosphonates and Arylphosphonates", filed Jun. 30, 1993), 3'-O-methylphosphonate (Jaworskamaslanka et al., *Antisense & Nucleic Acid Drug Development*, 1997, 7, 23–30), or -3'-O-methylphosphonothioate (International Patent Application PCT/US93/06277, entitled "Pentavalent synthesis of Oligonucleotides Containing Stereospecific Alkylphosphonates and Arylphosphonates", filed Jun. 30, 1993) before their stereoselective incorporation in the oligonucleotide.

The incorporation of alkylphosphonate internucleoside linkages into modified oligonucleotide has been limited to only a few groups. The primary group that has been used is the methylphosphonate group. The use of benzylphosphonate internucleotide linkages is another group that has been synthesized (Eisenhardt et al., *Nucleosides & Nucleotides*, 1997, 16, 1669–1672).

The synthesis of a T-T dimer having a phosphorothioate internucleoside linkage has been previously reported using chiral auxiliary indole-oxazaphosphorine with 3'-OTBDPS-thymidine in the presence of several equivalents of 1,8-diazabicyclo[5.40]undec-7-ene (DBU) (Wang, J. C., Just, G., *Tetrahedron Lett.*, 1997, 38, 3797–3800). After removal of the chiral auxiliary and sulfurization, the T-T phosphorothioate dimer is isolated in very high diastereomeric excess.

There remains a need for improved methods for preparing alkylphosphonates. There is further need for methods for preparing alkylphosphonates that are substantially diastereomerically pure or enriched. The present invention is directed to these, as well as other, important ends.

SUMMARY OF THE INVENTION

The present invention provides processes for preparing alkylphosphonate compounds having the structure:

wherein each $M_1$ and $M_2$ independently, are hydrogen or a hydroxyl protecting group or one of $M_1$ and $M_2$ is hydrogen or a hydroxyl protecting group and the other of $M_1$ and $M_2$ is a covalent attachment to a solid support. In the foregoing structure, each J is, independently, hydrogen, a 2'-substituent group, or a protected 2'-substituent group and $R_1$ is an electron withdrawing group. In such compounds, $X_2$ is hydrogen or —$(CH_2)_m$—$E_2$; $E_2$ is hydrogen, alkyl, aryl, aralkyl, substituted aryl, a heterocycle, mixed heterocycle or heteroaryl and m is 0, 1, 2 or 3. Each Bx is a heterocyclic base moiety, preferably of the type associated with nucleobases, such as the preferred purines and pyrimidines. The methods comprise the steps of selecting a dimeric trialkylphosphite compound of the structure:

and treating said dimeric trialkylphosphite compound, in a solvent, with a base under conditions of time temperature and pressure to form said alkylphosphonate compound.

It is preferred that one of $M_1$ and $M_2$ be a hydroxyl protecting group and the other of $M_1$ and $M_2$ be a covalent attachment to a solid support. In other preferred embodiments, both of $M_1$ and $M_2$ are hydroxyl protecting groups. It is preferred for some embodiments, that the electron withdrawing group be CN, $COOR_5$ wherein $R_5$ is $C_1$–$C_8$ alkyl, $NO_2$, $CF_3$, aryl, halogen or substituted aryl wherein said substituents are halogen, cyano, $C_1$–$C_6$ alkyl, perhalo $C_1$–$C_3$, alkyl, alkoxy, nitro, nitroso or carboxylate, with CN or $NO_2$ being more preferred. In some preferred embodiments, $X_2$ is H and $R_1$ is CN.

In the processes of the invention, the alkylphosphonate compound is prepared as substantially a single diastereomer. It is also preferred that the dimeric trialkylphosphite compound be substantially diastereomerically pure as well.

In accordance with some embodiments, it has been found useful for the base to be 1,8-diazabicyclo[5.40]undec-7-ene (DBU), diisopropylethylamine (Hunig's base), a secondary amine, piperidine, morpholine, or piperazine. It is preferred that the solvent be DMF, DMSO, THF, THP or $CH_3CN$.

In accordance with other embodiments, the processes of the invention further comprise treating the alkylphosphonate compound with a chemical compound under conditions of time, temperature and pressure effective to reduce or modify said electron withdrawing group and optionally treating said alkylphosphonate compound having said reduced or modified electron withdrawing group with a chemical functional group having a reactive moiety thereon, to form an alkylphosphonate compound of the structure:

wherein each $M_1$ and $M_2$ independently, are hydrogen or a hydroxyl protecting group or one of $M_1$ and $M_2$ is hydrogen or a hydroxyl protecting group and the other of $M_1$ and $M_2$ is a covalent attachment to a solid support. J is, independently, hydrogen, a 2'-substituent group or a protected 2'-substituent group, while $R_2$ is a group having the formula —$(CH_2)_m N(R_3)(R_4)$, —$N(R_3)(R_4)$, or —$C(O)N(R_3)(R_4)$. Each $R_3$ and $R_4$ independently, are H, $C_1$–$C_{10}$ alkyl, $C_1$–$C_{10}$ alkylamino, $C_1$–$C_{10}$ alkyl substituted alkylamino or a nitrogen protecting group; each $X_2$ is hydrogen or —$(CH_2)_m$—$E_2$; and $E_2$ is hydrogen, alkyl, aryl, aralkyl, substituted aryl, a heterocycle, mixed heterocycle or heteroaryl. It is preferred that each m be, independently, 0, 1, 2 or 3; and that Bx be a heterocyclic base moiety.

In the foregoing processes, the chemical compound is preferably a reducing agent, especially $BH_3.SMe_2$, $NaBH_4$ and $CoCl_2.6H_2O$, or $LiBH_4/MeOH$ and diglyme. In other embodiments, $X_2$ is H and $R_2$ is —$CH_2N(H)(R_3)$ where $R_3$ is $C_1$–$C_{10}$ alkyl. The chemical compound is preferably ammonia, a primary amine or a secondary amine wherein the substituents are $C_1$–$C_{10}$ alkyl, such as methylamine, dimethylamine, or dimethylaminoethlyamine.

The invention also features processes for preparing an alkylphosphonate compound of the structure:

wherein
each $M_1$ and $M_2$ independently, are hydrogen or a hydroxyl protecting group or one of $M_1$ and $M_2$ is hydrogen or a hydroxyl protecting group and the other of $M_1$ and $M_2$ is a covalent attachment to a solid support. Preferably, each J is, independently, hydrogen, a 2'-substituent group, or a protected 2'-substituent group; $R_1$ is an electron withdrawing group;

$X_2$ is hydrogen or —$(CH_2)_m$—$E_2$; and $E_2$ is hydrogen, alkyl, aryl, aralkyl, substituted aryl, a heterocycle, mixed heterocycle or heteroaryl. M is preferably 0, 1, 2 or 3; and Bx is a heterocyclic base moiety. The processes comprise the steps of: selecting an H-phosphonate compound of the structure:

and treating said H-phosphonate compound with an α,β-unsaturated compound of the structure:

in a solvent under conditions of time temperature and pressure to form said alkylphosphonate compound. In preferred embodiments, the H-phosphonate compound is treated with a silylating agent under conditions of time temperature and pressure to form a silyl intermediate prior to said treatment with said α,β-unsaturated compound. Preferably, the silylating agent is N,O-bis(trimethylsilyl)trifluoroacetamide, trimethylsilyl chloride in pyridine, 1-trimethylsilyl imidazole, 3-TMS-2-oxazolidinone, 1-TMS-1,2,4-triazole, or Bis-TMS urea.

It is preferred that one of $M_1$ and $M_2$ be a hydroxyl protecting group and the other of $M_1$ and $M_2$ is a covalent attachment to a solid support, although both of $M_1$ and $M_2$ can be hydroxyl protecting groups. It is preferred that the alkylphosphonate compound be prepared as substantially a single diastereomer and that the trialkylphosphite, itself, be substantially diastereomerically pure.

Alkylphosphonate compound can also be prepared in accordance with the invention by starting with a cyclic phosphoramidite compound of the structure:

wherein said $E_1$ is covalently attached to P by a N—P bond of said nitrogen containing heterocycle, nitrogen containing mixed heterocycle or nitrogen containing heteroaryl moiety to P. The cyclic structure is then treated with a base under conditions of time temperature and pressure to form an intermediate compound. The intermediate compound is then reacted with a further compound of the structure:

under conditions of time, temperature and pressure to form the alkylphosphonate compound.

The present invention also provides compounds of the structure:

wherein
Each $M_3$ and $M_4$ independently, are OH, a protected hydroxyl, a linkage to a solid support, an activated phosphate group, an activated phosphite group, a reactive group for forming an internucleotide linkage, a nucleotide, a nucleoside, or an oligonucleotide. Each J is, independently, hydrogen or a 2'-substituent group; $R_6$ is an electron withdrawing group or a group having the formula —$(CH_2)_n N(R_3)(R_4)$; each $R_3$ and $R_4$ independently, are H, $C_1$–$C_{10}$ alkyl or a nitrogen protecting group; and each $X_2$ is hydrogen or $—(CH_2)_n—$ $E_2$. $E_2$ is hydrogen, alkyl, aryl, aralkyl, substituted aryl, a heterocycle, mixed heterocycle or heteroaryl; n is 1, 2, or 3; and Bx is a heterocyclic base moiety.

DESCRIPTION OF PREFERRED EMBODIMENTS

The present invention provides novel dimeric and oligomeric compounds having alkylphosphonate internucleoside linkages and methods for their synthesis. The methods include the incorporation of substantially diastereomerically pure alkylphosphonate internucleoside linkages into dimers and oligomers of the invention. The methods also include the attachment of conjugate groups to alkylphosphonate internucleoside linkages. The treatment of a cyclic phosphoramidite, a trialkylphosphite, or an H-phosphonate with a selected base in a solvent followed by a further nucleoside in the case of the cyclic phosphoramidite or an α,β-unsaturated compound having an electron withdrawing group in the case of an H-phosphonate compound, will form the respective alkylphosphonate nucleoside dimer. The alkylphosphonate nucleoside dimer can be coupled to further nucleosides, oligonucleosides or oligonucleotides to give extended oligomeric compounds.

While not intending to be bound, the mechanism of the present methods is believed to involve the nucleophilic attack by a $P^{III}$ phosphorus species on the β carbon of an α,β-unsaturated compound. The α,β-unsaturated compound includes an electron withdrawing group conjugated to the α,β-unsaturated system which is capable of stabilizing the intermediate in the nucleophilic reaction leading to formation of the alkylphosphonate compound. The general mechanism of nucleophilic addition of the $P^{III}$ species to the α,β-unsaturated system including the role of the electron withdrawing group is illustrated below:

According to the above mechanism, a nucleophilic reagent (Z⁻) attacks the β-carbon of the α,β-unsaturated carbonyl system to form an intermediate ion in which the negative charge is partly accommodated by the electron withdrawing (electronegative) group (G). The ion obtains a proton and forms the saturated adduct.

Figure 1:
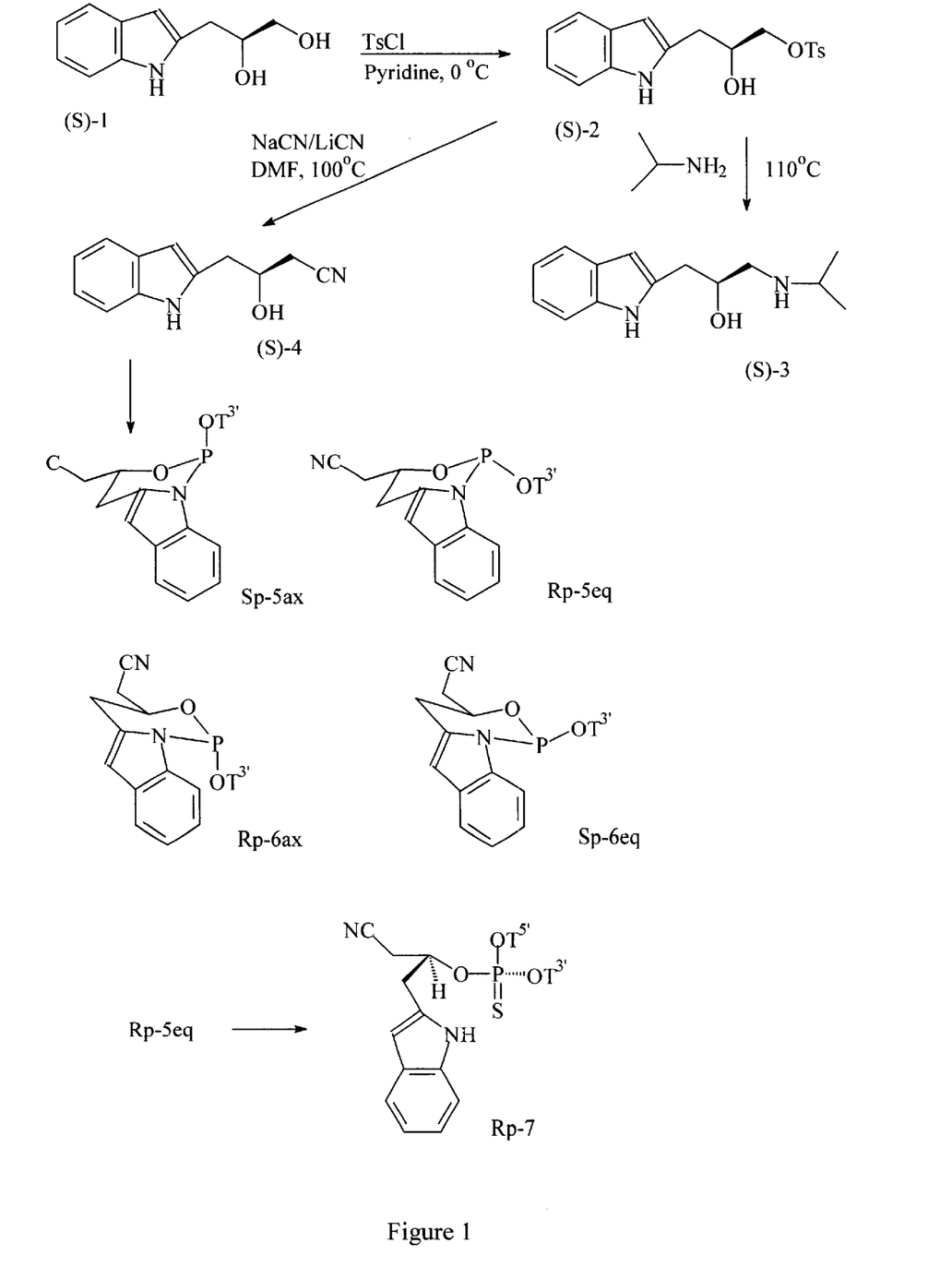
FIG. 1 is a synthetic scheme for the preparation of a protected phosphorothioate dimer (Rp-7).
Figure 2:
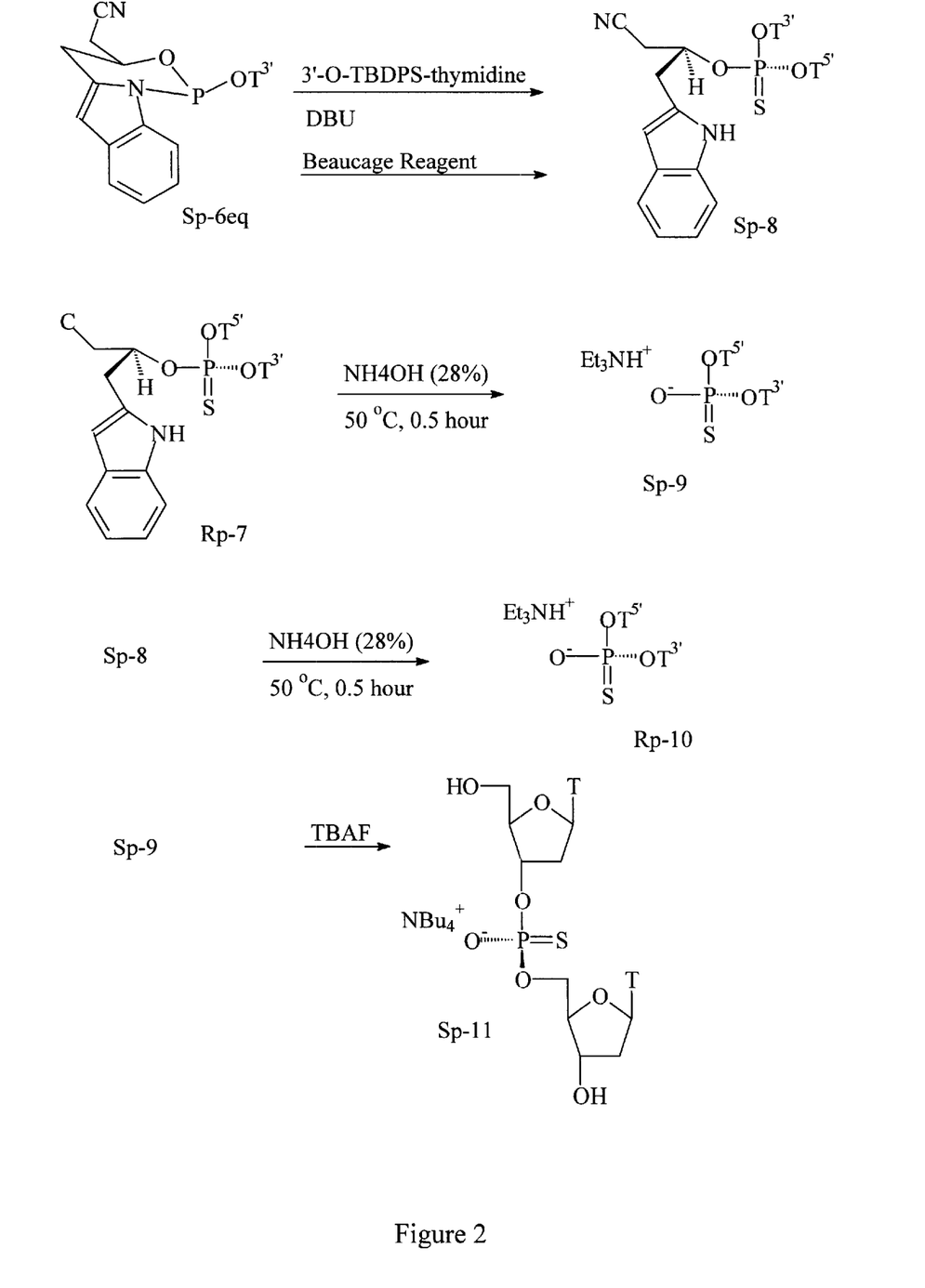
FIG. 2 is a synthetic scheme for the preparation of a phosphorothioate dimer as a salt (Sp-1).
Figure 3:
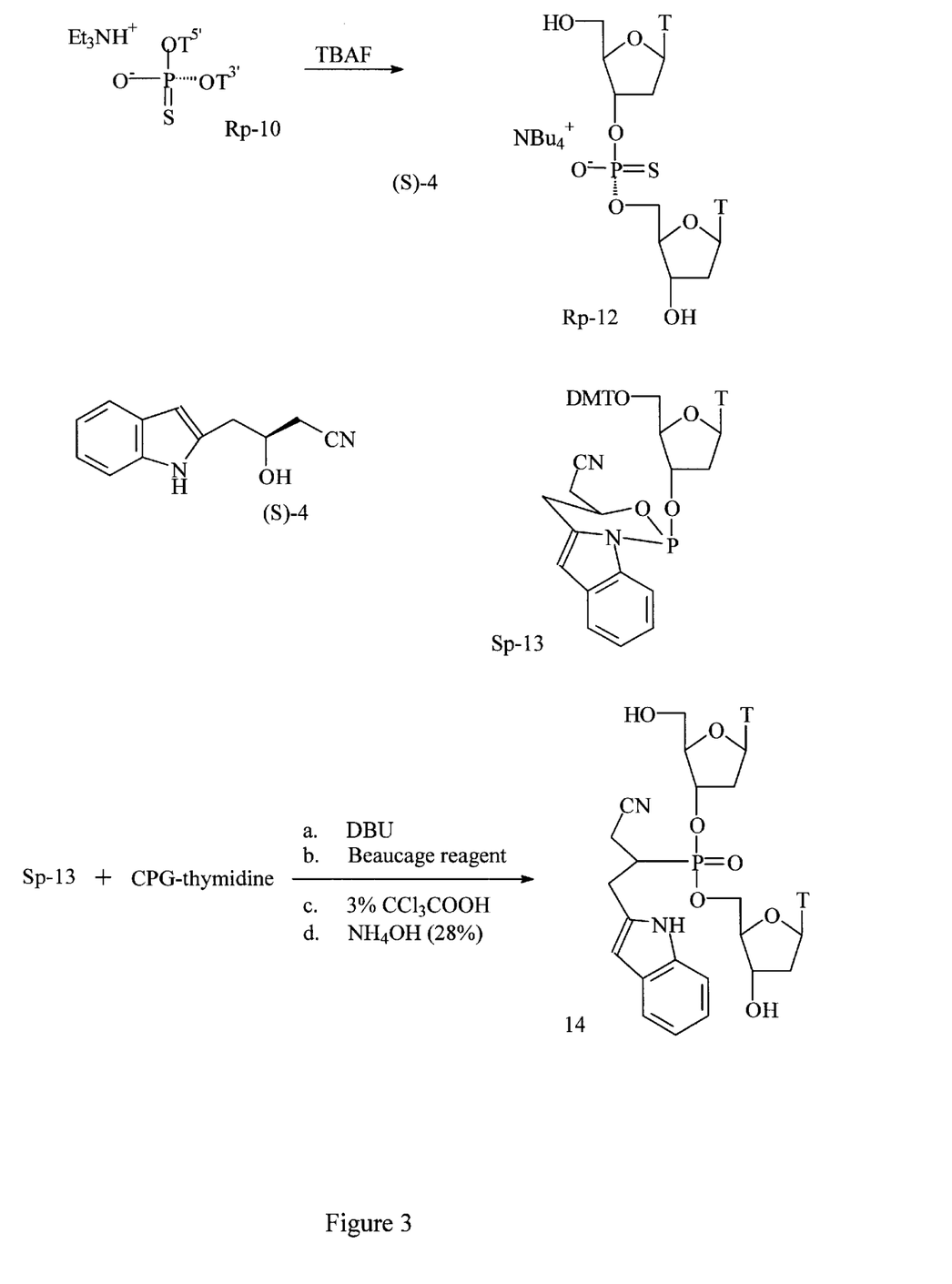
FIG. 3 is a synthetic scheme for the preparation of a phosphorothioate dimer (Sp-13) from the corresponding salt and for the synthesis of an alkylphosphonate dimer from chiral starting material and a solid support bound nucleoside (14).
Figure 4:
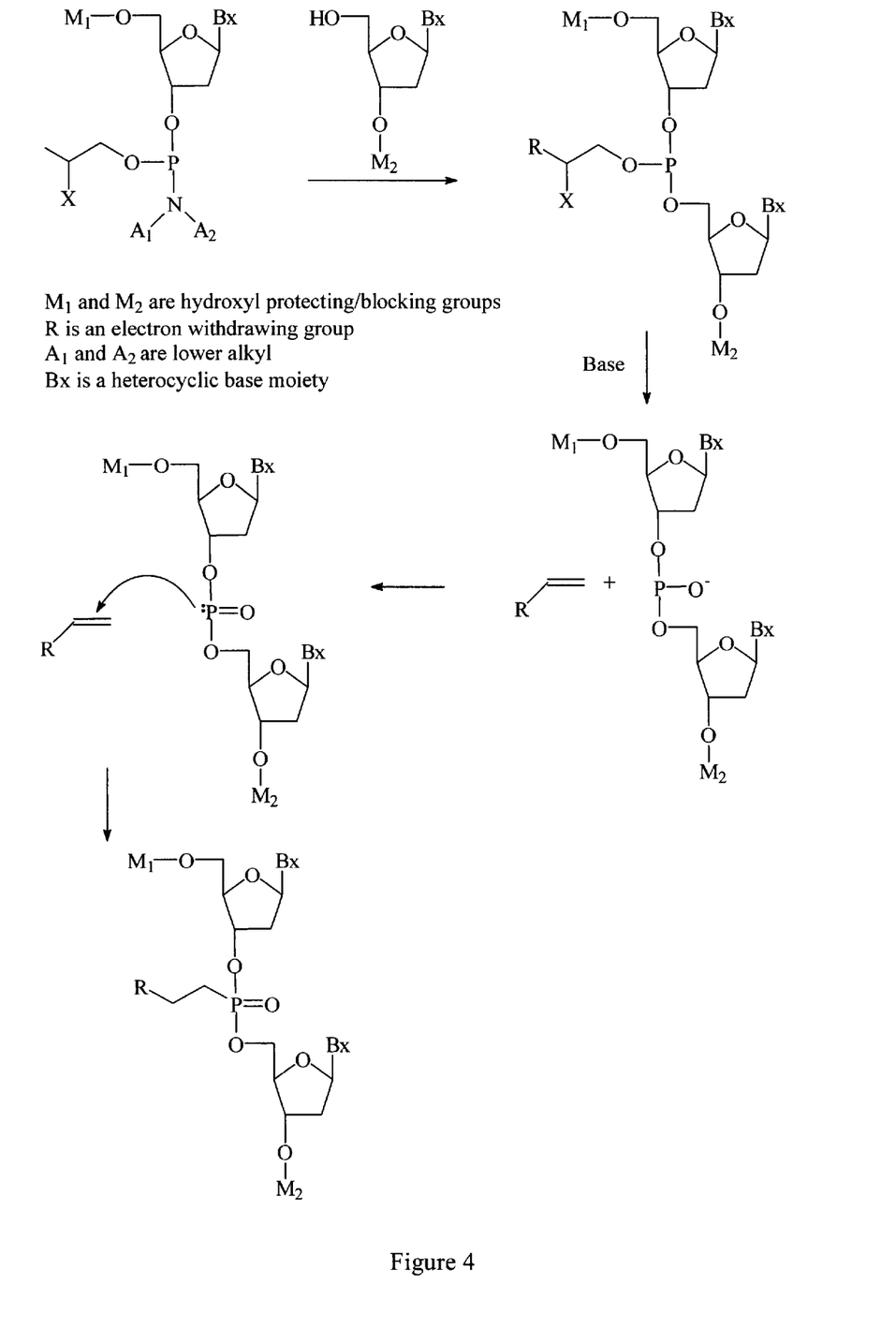
FIG. 4 is a synthetic scheme for the preparation of 3' and 5' protected alkylphosphonate dimers (15 and 16).

The methods of present invention are believed to share the above scheme in the final formation of the alkylphosphonate internucleoside linkage, however the source of the α,β-unsaturated compound depends on the starting material used. When the starting material is a trialkylphosphite or a cyclic phosphoramidite, the α,β-unsaturated compound is initially saturated and attached to the $P^{III}$ species through an oxygen atom. The treatment of either with a base such as DBU will cause β-elimination of the non-nucleosidic alkylphosphite group which forms the α,β-unsaturated compound. The base abstracts a proton from the saturated species causing cleavage of the carbon to oxygen bond and formation of the α,β-unsaturated compound. When a dimer having an H-phosphonate internucleoside linkage is the starting material the α,β-unsaturated compound has to be added to the reaction as it is not generated in situ as with the above starting materials. The overall process utilizing a phosphoramidite as the starting material is illustrated in FIG. 4.

In a preferred embodiment of the invention, the formation of alkylphosphonate internucleotide linkages occurs stereospecifically or stereoselectively. The stereoselectivity of the present methods was demonstrated in one study by comparison of the $^{31}P$ NMR spectra of phosphite dimer starting material and final product dimer formed therefrom. A trialkylphosphite dimer (5'-O-DMT-T-T-3'-O-TBDMS, Example 18) was prepared having a cyanoethoxy protecting group on the phosphorus. The dimer was purified; the purest fraction contained a mixture of diastereomers with one eluting faster than the other in a ration 1:10 ($^{31}P$ NMR: 140.0 ppm for the fast eluted, 139.8 ppm for the slow eluted). This mixture was dissolved in $CH_2Cl_2$ and treated with 10 equivalents of DBU at room temperature leading, after 10 hours, to the formation of the expected alkylphosphonate diastereomers. The ratio of the product diastereomers was identical to the ratio (1:10) of the starting diastereomers ($^{31}P$ NMR: 28.4 ppm for the fast eluted, 27.6 ppm for the slow eluted).

In two related studies, the diastereomeric products of alkylphosphonate synthesis from predominantly all S or all R starting materials was compared. In separate reactions Rp-5eq (Example 6) and Sp-6eq (Example 7) were dissolved in $CDCl_3$ and the resulting solutions treated with DBU (5 eq). Rp-5eq was determined by $^{31}P$ NMR to exist as a mixture of diastereomers in a ratio of 40 to 1 with the R diastereomer predominant. The Sp-6eq was similarly determined to exist as a mixture of diastereomers in a ratio of 13 to 1 with the S diastereomer predominant. After several minutes two peaks were observed in the $^{31}P$ NMR at 32.55 ppm and 32.26 ppm with a ratio of 1:10 for the Rp-5eq reaction. Similar peaks were observed in the Sp-6eq run. These peaks around 32 ppm were not isolatable. Each solution was then treated with 3 O—O-tert-butyldiphenylsilyl-thymidine (1 eq). During the course of the reaction the peaks around 32 ppm disappeared and new peaks were observed around 29 ppm. After chromatography of each of the two mixtures the $^{31}P$ NMR's were compared. In each case there were observed 4 peaks resulting from 4 diastereomers.

| Diastereomer Ratio | ~29.88 δ ppm | ~29.63 δ ppm | ~28.93 δ ppm | ~28.79 δ ppm |
|---|---|---|---|---|
| Rp-5eq 40:1 | 13.5 | 1.0 | 10.8 | 139.9 |
| Sp-6eq 13:1 | 13.5 | 1.3 | 1.0 | 1.9 |

The stereoselectivity is clearly seen in the predominance for one diastereomer in each experiment. The absolute configuration of each diastereomer was not elucidated.

There are many electron withdrawing groups amenable to the present invention that are known to those skilled in the art. Electron withdrawing groups amenable to the present invention, as illustrated above, are able to stabilize the intermediate that occurs upon nucleophilic attack by phosphorus. A representative list which is not meant as limiting includes CN, COOR$_5$ where R$_5$ is $C_1$–$C_8$ alkyl, NO$_2$, CF$_3$, aryl, halogen or substituted aryl wherein said substituents are halogen, cyano, $C_1$–$C_6$ alkyl, perhalo $C_1$–$C_3$, alkyl, alkoxy, nitro, nitroso or carboxylate.

In one embodiment, alkylphosphonate compounds according to the invention are reduced and optionally protected or further functionalized with a reactive chemical functional group. It is preferred that reactive chemical functional groups each have a leaving group that imparts sufficient reactivity to the chemical functional group making it reactive with a reduced electron withdrawing group.

Reducing agents according to the present invention are effective to selectively reduce an electron withdrawing group located on an alkylphosphonate compound but inert to other functional groups thereon. The choice of the reducing agent will depend on the nature of the electron withdrawing group and other groups present on the alkylphosphonate compound. Generally, the reduction of an electron withdrawing group uses a mild as opposed to strong reducing agent. A representative cyano reducing agent is $BH_3.SMe_2$. A representative nitro reducing agents are $NaBH_4$, $CoCl_2.6H_2O$ or $LiBH_4$, MeOH and diglyme. Esters are easily converted to amides with amines such as ammonia, methylamine, dimethylamine, or dimethylaminoethlyamine. Further reducing agents amenable to the present invention are disclosed in, Larock, R. C.; *Comprehensive Organic Transformations: a guide to functional group preparations;* VCH:New York, 1989; p 411–415.

Bases according to the present invention are essentially a reagent capable of abstracting an a-proton next to an electron withdrawing group of an α,β-unsaturated system such as illustrated above. Many bases are known to the art skilled that would suffice for this purpose. A representative list of bases that are amenable include 1,8-diazabicyclo[5.40]undec-7-ene (DBU), diisopropylethylamine (Hunig's base), a secondary amine, piperidine, morpholine, or piperazine.

Silylating agents according to the invention are those that can react with a hydroxyl group and form a silyl intermediate. The silylating agents may enhance the conversion of H-phosphonate internucleoside linkages to the corresponding alkylphosphonate internucleotide linkage in the presence of an α,β-unsaturated compound. Representative examples of silylating agents that are amenable to the present invention include N,O-bis(trimethylsilyl)trifluoroacetamide, trimethylsilyl chloride in pyridine, 1-trimethylsilyl imidazole, 3-TMS-2-oxazolidinone, 1-TMS-1,2,4-triazole, and Bis-TMS urea (TMS=trimethylsilyl).

The methods according to the present invention are performed in various traditional solvents either utilizing solution phase techniques or automated synthetic protocols. Many solvents for automated oligonucleotide synthesis as well as solution phase oligonucleotide synthesis are known in the art. Preferred solvents include DMF, DMSO, THF, THP or $CH_3CN$.

Standard solution phase and solid phase methods for the synthesis of oligonucleotides and oligonucleotide analogs are well known to those skilled in the art. These methods are constantly being improved in ways that reduce the time and cost required to synthesize these complicated compounds. Representative solution phase techniques are described in U.S. Pat. No. 5,210,264, issued May 11, 1993 and commonly assigned with this invention. Representative solid phase techniques employed for oligonucleotide and oligonucleotide analog synthesis utilizing standard phosphoramidite chemistries are described in, Protocols For Oligonucleotides And Analogs, Agrawal, S., ed., Humana Press, Totowa, N.J., 1993.

A representative list of chemical functional groups according to the invention include H, $C_1$–$C_{10}$ alkyl; substituted alkyl; $C_2$–$C_{10}$ alkenyl; substituted alkenyl; $C_2$–$C_{10}$ alkynyl; substituted alkynyl; $C_4$–$C_7$ carbocyclic alkyl; substituted carbocyclic alkyl; alkenyl carbocyclic; substituted alkenyl carbocyclic; alkynyl carbocyclic; substituted alkynyl carbocyclic; $C_6$–$C_{14}$ aryl; substituted $C_6$–$C_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from alkyl, alkenyl, alkynyl, aryl, hydroxyl, alkoxy, alcohol, benzyl, nitro, thiol, thioalkyl, thioalkoxy, or halogen groups; or L is phthalimido, an ether having 2 to 10 carbon atoms and 1 to 4 oxygen or sulfur atoms, a metal coordination group, a conjugate group, halogen, hydroxyl, thiol, keto, carboxyl, $NR^1R^2$, $CONR^1$, amidine ($C(=NH)NR^2R^3$), guanidine ($NHC(=NH)NR^2R^3$), glutamyl ($R^1OOCCH(NR^2R^3)(CH_2)_2C(=O)$), nitrate, nitro, nitrile, trifluoromethyl, trifluoromethoxy, NH-alkyl, N-dialkyl, O-aralkyl, S-aralkyl, NH-aralkyl, azido ($N_3$), hydrazino ($NHNH_2$), hydroxylamino ($ONH_2$), sulfoxide (SO), sulfone ($SO_2$), sulfide (S—), disulfide (S—S), silyl, a nucleosidic base, an amino acid side chain, a carbohydrate, a drug, or a group capable of hydrogen bonding. Where each $R^1$ and $R^2$ is, independently, H, alkyl or haloalkyl having 1 to about 10 carbon atoms, alkenyl having 2 to about 10 carbon atoms, alkynyl having 2 to about 10 carbon atoms, or aryl having 6 to about 14 carbon atoms; and each $R^3$ is, independently, a single bond; CH=CH; C≡C; O; S; $NR^6$; $SO_2$; $C_6$–$C_{14}$ aryl; substituted $C_6$–$C_{14}$ aryl; heteroaryl; substituted heteroaryl; a nitrogen, oxygen, or sulfur containing heterocycle; a substituted nitrogen, oxygen, or sulfur containing heterocycle; a mixed heterocycle; or a substituted mixed heterocycle; where said substituent groups are selected from hydroxyl (OH), alkoxy, alcohol, benzyl, phenyl, nitro ($NO_2$), thiol (SH), thioalkoxy, halogen, alkyl, aryl, alkenyl, and alkynyl groups.

Heterocyclic base moieties amenable to the present invention include both naturally and non-naturally occurring nucleobases and heterocycles. A representative list includes adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further heterocyclic bases include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch, et al., *Angewandte Chemie, International Edition* 1991, 30, 613.

In the context of this invention, a heterocycle is a cyclic compound containing at least one hetero atom such as N, O, or S. A mixed heterocycle is a cyclic compound containing at least two hetero atoms such as N, O, or S. A heteroaryl compound is a heterocycle containing at least one hetero atom such as N, O, or S and is not fully saturated e.g is in a state of partial or complete saturation. Heteroaryl is also meant to include fused systems including systems where one or more of the fused rings contain no heteroatoms. Heterocycles, including nitrogen heterocycles, according to the present invention include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, indole, and carbazole groups.

A number of chemical functional groups can be introduced into compounds of the invention in a blocked form and subsequently deblocked to form a final, desired compound. In general, a blocking group renders a chemical functionality of a molecule inert to specific reaction conditions and can later be removed from such functionality in a molecule without substantially damaging the remainder of the molecule (Green and Wuts, Protective Groups in Organic Synthesis, 2d edition, John Wiley & Sons, New York, 1991). For example, amino groups can be blocked as phthalimido groups, as 9-fluorenylmethoxycarbonyl (FMOC) groups, and with triphenylmethylsulfenyl, t-BOC or benzyl groups. Carboxyl groups can be protected as acetyl groups. Representative hydroxyl protecting groups are described by Beaucage et al., *Tetrahedron* 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl) xanthine-9-yl (MOX). Chemical functional groups can also be "blocked" by including them in a precursor form. Thus, an azido group can be used considered as a "blocked" form of an amine since the azido group is easily converted to the amine. Further representative protecting groups utilized in oligonucleotide synthesis are discussed in Agrawal, et al., Protocols for Oligonucleotide Conjugates, Eds, Humana Press; New Jersey, 1994; Vol. 26 pp. 1–72.

In one aspect of the invention, conjugate groups are attached to the alkylphosphonate internucleoside linkage of dimeric and oligomeric compounds. As illustrated in Example 26, cholesterol is attached to the amino propylphosphonate internucleoside linkage of a dimer. There are many conjugate groups known to the art skilled that are amenable to the present invention. A representative list of conjugate groups of the invention include intercalators, reporter molecules, polyamines, polyamides, poly ethers including polyethylene glycols, and other moieties known in the art for enhancing the pharmacodynamic properties or the pharmacokinetic properties. Typical conjugate groups include PEG groups, cholesterols, phospholipids, biotin, phenanthroline, phenazine, phenanthridine, anthraquinone, acridine, fluoresceins, rhodamines, coumarins, and dyes.

As used herein the term "2'-substituent group" includes groups attached to the 2' position of the ribosyl moiety with or without an oxygen atom. 2'-Sugar modifications amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249, each of which are hereby incorporated by reference in their entirety. Further sugar modifications are disclosed in Cook, P. D., *Anti-Cancer Drug Design*, 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Additional 2' sugar modifications amenable to the present invention include 2'-SR and 2'-NR$_2$ groups, where each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.*, 1997, 62, 3415–3420. 2'-NR$_2$ nucleosides are disclosed by Goettingen, M., *J. Org. Chem.*, 1996, 61, 6273–6281; and Polushin et al., *Tetrahedron Lett.*, 1996, 37, 3227–3230. Further representative 2'-O-sugar modifications amenable to the present invention include those having one of formula I or II:

wherein

E is C$_1$–C$_{10}$ alkyl, N(R$_4$)(R$_5$) or N=C(R$_4$)(R$_5$);

each R$_4$ and R$_5$ is, independently, H, C$_1$–C$_{10}$ alkyl, a nitrogen protecting group, or R$_4$ and R$_5$, together, are a nitrogen protecting group or wherein R$_4$ and R$_5$ are joined in a ring structure that can include at least one additional heteroatom selected from N and O.

R$_3$ is OX, SX, or N(X)$_2$;

each X is, independently, H, C$_1$–C$_8$ alkyl, C$_1$–C$_8$ haloalkyl, C(=NH)N(H)Z, C(=O)N(H)Z or OC(=O)N(H)Z;

Z is H or C$_1$–C$_8$ alkyl;

L$_1$, L$_2$ and L$_3$ comprise a ring system having from about 4 to about 7 carbon atoms or having from about 3 to about 6 carbon atoms and 1 or 2 hetero atoms wherein said hetero atoms are selected from oxygen, nitrogen and sulfur and wherein said ring system is aliphatic, unsaturated aliphatic, aromatic, or saturated or unsaturated heterocyclic;

Y is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_4)(R_5)$ $OR_4$, halo, $SR_4$ or CN;

each $q_1$ is, independently, from 2 to 10;

each $q_2$ is, 0 or 1;

p is from 1 to 10; and r is from 1 to 10 with the proviso that when p is 0, r is greater than 1.

Representative 2'-O-sugar substituents of formula I are disclosed in U.S. patent application Ser. No.: 09/130,973, filed Aug. 7, 1998, entitled Capped 2'-Oxyethoxy Oligonucleotides, hereby incorporated by reference in its entirety.

Representative cyclic 2'-O-sugar substituents of formula II are disclosed in U.S. patent application Ser. No.: 09/123,108, filed Jul. 27, 1998, entitled RNA Targeted 2'-Modified Oligonucleotides that are Conformationally Preorganized, hereby incorporated by reference in its entirety.

Further in the context of this specification aryl groups (generally $C_6$–$C_{20}$) include but are not limited to substituted and unsubstituted aromatic hydrocarbyl groups. Aralkyl groups (generally $C_7$–$C_{20}$) include but are not limited to groups having both aryl and alkyl functionalities, such as benzyl and xylyl groups. Preferred aryl and aralkyl groups include, but are not limited to, phenyl, benzyl, xylyl, naphthyl, toluyl, pyrenyl, anthracyl, azulyl, phenethyl, cinnamyl, benzhydryl, and mesityl. Typical substituents for substitution include, but are not limited to, hydroxyl, alkoxy, alcohol, benzyl, phenyl, nitro, thiol, thioalkoxy, halogen, or alkyl, aryl, alkenyl, or alkynyl groups.

Additional objects, advantages, and novel features of the present invention will become apparent to those skilled in the art upon examination of the following examples thereof The following examples illustrate the invention and are not intended to limit the same. Those skilled in the art will recognize, or be able to ascertain through routine experimentation, numerous equivalents to the specific substances, compositions, and procedures described herein. Such equivalents are considered to be within the scope of the present invention.

EXAMPLES

General Methods

Melting points (m.p.) were determined on a GallenKamp block and are uncorrected.

$^1$H-NMR spectra were recorded on a Varian XL-200, JEOL 270 or Varian UNITY 500 spectrometer at 200, 270 and 500 MHZ respectively. Peak assignments are based on 2D-correlation spectroscopy (COSY).

13C-NMR spectra were recorded on a Varian XL-300, JEOL CFP 270 or Varian UNITY 500 spectrometer at 75.4, 67.9 and 125.7 MHZ. Peak assignments were made with the help of 2D-heteronuclear multiple quantum coherence (HMQC) spectroscopy. $^{31}$P-NMR spectra were recorded on JEOL CFP 270, Varian XL-300, or Varian UNITY 500 at 109.4, 121.42 and 202.3 MHZ using 85% $H_3PO_4$ as an external standard.

Low resolution chemical ionization (CI-MS), electron ionization (EI-MS) mass spectra and fast atom bombardment (FAB-MS) were obtained on an KRATOS MS 25RFA spectrometer in the direct-inlet mode. High resolution FAB mass spectra of key compounds were obtained on a ZAB 2F HS spectrometer in the direct inlet mode (Biomedical Spectrometry Unit).

Thin layer chromatography (TLC) was performed using Kieselgel 60 $F_{254}$ aluminum backed plates (0.2 mm thickness). Preparative plate thin layer chromatography (pTLC) was performed using Kieselgel 60 $F_{254}$ glass backed plates (0.5 and 1.0 mm thickness). Spot(s) were visualized by UV, or by dipping in a solution of ammonium molybdate (2.5 g) and ceric sulfate (1.0 g) in 10% v/v aqueous sulfuric acid (100 mL) followed by heating, or by dipping into a 1% (w/v) aqueous solution of ninhydrin followed by heating.

HPLC: HP 1090 Series II with Waters C-4 column (3.9× 300 mm), Varian Vista 5500 with Chiralcel OD column (4.6×250 mm). Optical rotations were recorded on a Jasco DIP-140 digital polarimeter.

Tetrahydrofuran (THF) was dried by distillation on sodium benzophenone ketyl, dichloromethane on phosphorus pentoxide, methanol on magnesium, triethylamine and $CH_3CN$ on calcium hydride, pyridine on barium oxide. Dry DMF was purchased from Aldrich Chemical Company Inc. in sure-seal bottles and was used without further drying.

Phosphorus trichloride was first degassed by refluxing for 2 hours under argon followed by fractional distillation and was stored under argon. DBU and isopropanol were purified by fractional distillation then stored over 4 Å Linde molecular sieves under argon. All other chemicals were purchased from Aldrich Chemical Company Inc., Sigma Chemicals, or Fluka Chemicals and used without further purification unless specified. 3'-O-TBDPS-thymidine, solid support (CPG) and Beaucage reagent were purchased from Glen Research, Sterling Va.

Example 1

(S)-3-Indol-2-yl-2-hydroxypropyl p-toluenesulfonate (S)-2

To a solution of (S)-3-indol-2-yl-propane-1,2-diol (S)-1 (15 g, 78.5 mmol) in dry pyridine (120 mL) was added p-toluenesulfonyl chloride (15.5 g, 81.3 mmol) at 0° C. After stirring for 5 hours at 0° C., the solution was poured into cold hydrochloric acid (100 mL, 6N) and extracted with ether (3×60 mL). The combined extracts were washed with hydrochloric acid (6N, 2×30 mL) followed by brine (2×80 mL) and dried over anhydrous sodium sulfate. The solvent was evaporated and the residue was purified by flash chromatography to give 24.5 g (90.4%) of the title compound as a white solid.

M.p. 96–97° C.. $[a]^D_{295}$ +0.93° 1.0, ethyl acetate. $^1$H NMR (500 MHZ, $CDCl_3$): 8.51 (s, broad, 1H, NH), 7.78–7.06 (m, 8H, aromatic H), 6.21 (s, 1H, H-3-indole), 4.16 (m, 1H, CHO), 4.0 (m, 2H, $CH_2O$), 2.97 (m, 2H, $CH_2C$), 2.44 (s, 3H, $CH_3$). $^{13}$C NMR (125.7 MHZ, $CDCl_3$): 145.15, 136.09, 133.99, 132.17, 129.87, 127.78, 121.36, 119.75, 119.55, 110.56, 101.28, 72.49, 68.98, 31.27, 21.49. MS (CI, $NH_3$): 346 (M+H$^+$, 6.0%), 174 (100.0%).

Example 2

(R)-3-Indol-2-yl-2-hydroxypropyl p-toluenesulfonate (R)-2

Using the procedure illustrated in Example 1 above the title compound was prepared having the R-configuration. Hence, (R)-3-indol-2-yl-propane-1,2-diol (R)-1 (1.95 g, 10.2 mmol) provided 3.1 g (89%) of the title compound as a white solid.

M.p. 112–113° C.. $[a]^D_{295}$ –1.03° 1.035, ethyl acetate). $^1$H NMR (270 MHZ, $CDCl_3$): 8.52 (s, broad, 1H, NH), 7.77–7.03 (m, 8H, aromatic H), 6.19 (s, 1H, H-3-indole), 4.15 (m, 1H, CHO), 3.97 (m, 2H, $CH_2O$), 2.92 (m, 2H, $CH_2C$), 2.71 (d, J=4.5 Hz, 1H, OH), 2.42 (s, 3H, $CH_3$). $^{13}$C NMR (125.7 MHZ, $CDCl_3$): 145.40, 136.34, 134.29, 132.40, 130.11, 128.32, 128.02, 121.58, 119.99, 119.78, 110.83, 101.49, 72.77, 69.22, 31.54, 21.74. MS (FAB, NBA): 346 (M+H+, 80.5%).

Example 3

(S)-3-Indol-2-yl-1-isopropylamino-isopropanol (S)-3

To a pressure vessel was added sulfonate derivative (S)-2 (2.94 g) and isopropylamine (10 mL) with stirring at 110° C. overnight. Evaporation of the solvent afforded an amber oil which was purified by flash chromatography (acetone/triethylamine 10:1) to give 1.6 g (81%) of the title compound as a sticky solid.

$[a]^P_{295}$ −8.13° 0.75, ethyl acetate). $^1$H NMR (270 MHZ, CDCl$_3$): 9.01 (s, broad, 1H, NH), 7.0–7.5 (m, 4H, aromatic H), 6.23(s, 1H, H-3-indole), 3.89 (m, 1H, CHO), 2.72–3.03 (m, 5H, NCH, OH, NH, CH$_2$), 2.44, 2.59 (m, 2H, CH$_2$N), 1.05, 1.04 (d, 6H, $^3$J=6.18 Hz, (CH$_3$)$_2$). $^{13}$C NMR (67.9 MHZ, CDCl$_3$): 136.61, 136.28, 128.43, 121.12, 119.81, 119.46, 110.73, 100.68 (C$_8$H$_5$N), 69.37, 51.80, 49.04, 33.34, 23.12, 22.81. MS (CI, NH$_3$): 233 (M+H+, 100.0%), 130 (31.9%).

Example 4

(R)-3-hydroxy-4-(2-indolyl)butyronitrile (R)-4

To a solution of 0.5 M LiCN in DMF (30 mL) was added (R)-3-indol-2-yl-2-hydroxypropanyl p-toluenesulfonate (R)-2 (5.6 g, 16.2 mmol) and sodium cyanide (1.5 g, 30.6 mmol). The reaction mixture was stirred for 1 hour at 100° C., cooled to room temperature, poured into 80 mL ice-water, and extracted with ethyl acetate (3×50 mL). The combined organic solution was washed with saturated sodium bicarbonate (2×50 mL), brine (2×30 mL), dried over anhydrous sodium sulfate, and evaporated to yield a deep red oil. The oil was purified by flash chromatography (hexane:ethyl acetate 2:3) to give 2.4 g (74%) of the title compound as a light yellow solid.

The chirality of (R)-4 was analyzed by HPLC (Varian Vista 5500) with Chiralcel OD column (4.6×250 mm) in 1.5 mL/min flow rate of hexane:ethanol (9:1) and was 91% ee. (R)-4 (2.0 g) was dissolved in chloroform (2 mL), and the solvent was slowly evaporated at room temperature and atmospheric pressure. After a week, crystals were formed and filtered off, m.p. 92–93° C. The filtrate was collected and dried under vacuum to give (R)-4 (0.5 g) in 96% ee.

$[a]^P_{295}$ −8.67° 0.565, ethyl acetate). $^1$H NMR (500 MHZ, CDCl$_3$): δ8.37 (s, broad, 1H, NH), 7.5–7.0 (m, 4H, aromatic H), 6.32 (s, 1H, H-3-indole), 4.22 (m, 1H, CHO), 3.05, 2.96 (m, 2H, CH$_2$), 2.67 (s, br. 1H, OH), 2.49 (m, 2H, CH$_2$CN). $^{13}$C NMR (125.7 MHZ, CDCl$_3$): δ136.12, 133.37, 128.09, 121.71, 119.94, 119.81, 110.60, 101.82 (C$_8$H$_5$N), 117.21 (CN), 67.23 (CH$_2$C), 34.71 (CHO), 25.06 (CH$_2$CN). MS (EI): 200 (M+, 48.5%), 130 (100%).

Example 5

(S)-3-hydroxy-4-(2-indolyl)butyronitrile (S)-4

The title compound was prepared as per the procedure illustrated in Example 4 above using (S)-3-hydroxy-4-(2-indolyl)-butyronitrile (S)-2. (S)-2 (1.62 g, 4.7 mmol) was treated with sodium cyanide (0.5 g, 10.2 mmol) in a solution of LiCN (0.5 M in DMF, 20 mL). After purification 0.6 g (64%) of the title compound was obtained as a light yellow solid (m.p. 78–79° C.). The chirality was 85% ee and after recrystallization 96% ee, m.p. 93–94° C.

$[a]^P_{295}$ 7.67° 0.975, ethyl acetate). $^1$H NMR (270 MHZ, CDCl$_3$): 8.42 (s, broad, 1H, NH), 7.0–7.5 (m, 4H, aromatic H), 6.30 (d, 1H, $^4$J=1.48 Hz, H-3-indole), 4.20 (m, 1H, CHO), 3.01 (m, 2H, CH$_2$), 2.47, 2.49 (m, 2H, CH$_2$CN). $^{13}$C NMR (67.9 MHZ, CDCl$_3$): 136.56, 133.58, 128.55, 121.94, 120.16, 120.06, 110.74, 102.12 (indole), 117.12 (CN), 67.55 (CH$_2$C), 35.10 (CHO), 25.28 (CH$_2$CN). MS (EI): 200 (59.6%, M+), 130 (100%, M−CNCH$_2$CH$_2$O).

Example 6

Rp-indole-oxazaphosphorine Sp-5ax-minor, Rp-5eq-major

A dry 5-mL round-bottomed flask containing dry THF (1 mL) was flushed with argon and sealed with a septum and PCl$_3$ (44 mL, 0.5 mmol) was introduced via a micro-syringe. The flask was cooled to −78° C. in a dry-ice/acetone bath, and a solution of (R)-3-hydroxy-4-(2-indolyl)butyronitrile (R)-4 (100 mg, 0.5 mmol) in THF (1 mL) containing triethylamine (0.3 mL, 2.2 mmol) was added via a syringe. The reaction mixture was stirred for 30 minutes at −78° C., then warmed up to 0° C. for an hour. The flask was cooled to −78° C. again, and a solution of 5-O'-tetrabutyldimethylsilyl(TBDMS)-thymidine (178 mg, 0.5 mmol) in THF (0.5 mL) was added via a syringe. The reaction mixture was stirred at −78° C. for 30 minutes, then the cooling bath was removed and the solution was warmed to room temperature. The triethylammonium chloride was filtered off and washed with CH$_2$Cl$_2$ (2×1 mL). The filtrate was concentrated and purified by thin layer chromatography (CH$_2$Cl$_2$:CH$_3$CN 2:10) to afford 94 mg (32%) of the title compound, a mixture of diastereoisomers, as a white solid (m.p. 85–86° C.).

The diastereoisomers (Rp-5, equitorial; and Sp-5, axial) were obtained in a ratio of 30:1 as established by $^{31}$P NMR. $^{31}$P NMR (202.3 MHZ, CDCl$_3$): δ Rp-5, 120.78 (96.8%), Sp-5 120.65 (3.2%).

NMR spectra were determined for the major diastereoisomer (Rp-5) as follows: $^1$H NMR (500 MHZ, CDCl$_3$): δ8.35 (br s, 1H, NH), 7.39 (s, 1H, H-6), 7.57–7.17 (m, 4H, aromatic H), 6.42 (s, 1H, H-3-indole), 6.32 (dd, 1H, $^3$J=8.8, 5.0 Hz, H-1'), 4.80 (m, 1H, H-3'), 4.52 (m, 1H, CHOP), 4.02 (m, 1H, H-4'), 3.65, 3.23 (m, 2H, HH'-5'), 3.40, 3.25 (m, 2H, CH$_2$C), 2.91,2.82 (m, 2H, CH$_2$CN), 2.38, 2.04 (m, 2H, HH'-2'), 1.87 (s, 3H, CH$_3$C-5), 0.85 (s, 9H, SiC(CH$_3$)$_3$), −0.004, −0.030 (d, 6H, Si(CH$_3$)$_2$). $^{13}$C NMR (125.7 MHZ, CDCl$_3$): δ163.37 (C-4), 149.97 (C-2), 134.95, 133.35, 129.42, 129.41, 122.58, 121.69, 120.45, 115.64, 110.87, 110.25, 110.16, 104.23, 85.78 (d), 84.39, 74.47 (d), 69.44 (d), 62.62, 39.93 (d), 30.63 (d), 25.68, 25.36 9d), 18.07, 12.29, −5.69, −5.92. MS (FAB, NBA): 585 (M+H+, 19.7%). HRMS (FAB, M+H+): C$_{28}$H$_{38}$N$_4$O$_6$PSi, Calcd. 585.229827, Found 585.229850.

Example 7

Sp-indole-oxazaphosphorine Rp-6ax-minor, Sp-6eq-major

A dry 25-mL round-bottomed flask containing dry THF (10 mL) was flushed with argon and sealed with a septum. PCl$_3$ (206 mL, 2.36 mmol) was introduced via a microsyringe. The flask was cooled to 0° C. in an ice-bath, and a solution of (S)-3-hydroxy-4-(2-indolyl)butyronitrile (472 mg, 2.36 mmol) in THF (2 mL) containing triethylamine (1.2 mL, 8.6 mmol) was added via a syringe. The reaction mixture was stirred for 30 minutes at 0° C., then warmed to room temperature for half an hour. The flask was cooled to 0° C. and a solution of 5-O'-TBDMS-thymidine (800 mg, 2.3 mmol) in $CH_2Cl_2$ (4 mL) was added via a syringe. The reaction mixture was stirred at 0° C. for 30 minutes. The byproduct triethylammonium chloride was filtered off and washed with $CH_2Cl_2$ (2×5 mL). The filtrate was concentrated and purified by silica gel chromatography ($CH_2Cl_2$:$CH_3CN$ 1:10) to afford 567 mg (41.2%) of the title compounds as a white solid.

M. p. 93–94° C. The two diastereoisomers of indole-oxazaphosphorine Sp-6ax and Rp-6eq were obtained in a ratio of 6:1 as established by $^{31}P$ NMR. $^{31}P$ NMR (202.3 MHZ, $CDCl_3$): δ Sp-6eq, 120.53 (85.3%), Rp-6ax, 120.72 (14.7%). The following NMR spectra were assigned for the major diastereoisomer.

$^1H$ NMR (500 MHZ, $CDCl_3$): δ9.20 (br s, 1H, NH), 7.42 (s, 1H, H-6), 7.57–7.17 (m, 4H, aromatic H), 6.42 (s, 1H, H-3-indole), 6.34 (dd, 1H, $^3J$=8.8, 5.0 Hz, H-1'), 4.82 (m, 1H, H-3'), 4.47 (m, 1H, CHOP), 3.94 (m, 1H, H-4'), 3.76, 3.66 (m, 2H, HH'-5'), 3.40–3.24 (m, 2H, $CH_2C$), 2.91 (m, 2H, $CH_2CN$), 2.41, 2.01 (m, 2H, HH'-2'), 1.89 (s, 3H, $CH_3C$-5), 0.88 (s, 9H, $SiC(CH_3)_3$), 0.066, 0.072 (d, 6H, $Si(CH_3)_2$). $^{13}C$ NMR (67.9 MHZ, $CDCl_3$): δ163.66 (C-4), 150.41 (C-2), 138.11, 137.87, 135.14, 133.60, 129.67, 122.78, 121.86, 120.75, 116.13, 111.18, 110.51, 110.35, 104.41, 86.41, 86.35, 84.81, 75.49, 75.30, 70.71, 70.59, 63.15, 39.82, 30.88, 30.80, 25.96, 18.36, 12.55, −5.30, −5.41. MS (FAB, NBA): 557 (M−HCN, 44.5%).

Example 8

Rp-(5'-O-TBDMS)thymid-3'-yl-(3'-O-TBDPS)-thymid-5'-yl-(R)-(1-cyano-3-indol-2-yl)isopropylphosphorothioate Rp-7

To a solution of indole-oxazaphosphorine Sp-6eq/Rp-6ax (30:1) (80 mg, 0.137 mmol) in dry THF (0.5 mL) was added 3'-O-TBDPS-thymidine ($T^{5'}OH$) (50 mg, 0.104 mmol) followed by DBU (40 mL, 0.268 mmol). The reaction mixture was shaken at room temperature for 10 minutes and passed though a short silica gel column to remove DBU. The column was eluted with $CH_3CN$ and the solvent was evaporated to afford a light yellow solid. The solid was dissolved in dry $CH_2Cl_2$ (2 mL), and Beaucage's reagent (35 mg, 0.175 mmol) was added. After 5 minutes, evaporation of the solvent followed by flash chromatography ($CH_2Cl_2$/$CH_3COCH_3$ 5:1) afforded 84 mg (74%) of the title compound as a light yellow solid.

M.p. 113–114° C. $^{31}P$ NMR (202.3 MHZ, $CDCl_3$): δ66.55 ppm. $^1H$ NMR (500 MHZ, $CDCl_3$): δ10.21, 9.56, 9.14 (3×s, br., 3H, NH-3-$T^{5'}$, NH-3-$T^{3'}$, NH-indole), 7.62–6.92 (m, 16H, aromatic H, H-6-$T^{3'}$, H-6-$T^{5'}$), 6.35 (m, 1H, H-1'-$T^{5'}$), 6.28 (s, 1H, H-3-indole), 6.06 (dd, 1H, $^3J$=9.0, 5.5 Hz, H-1'-$T^{3'}$), 4.88 (m, 1H, CHOP), 4.82 (m, 2H, H-3'-$T^{3'}$), 4.32 (m, 1H, H-3'-$T^{5'}$), 4.06 (m, 1H, H-4'-$T^{5'}$), 3.93 (m, 1H, H-4'-$T^{3'}$), 3.88 (m, 1H, H-5'-$T^{5'}$), 3.71 (m, 2H, H-5'-$T^{3'}$, H'-5'-$T^{5'}$), 3.63 (m, 1H, H'-5'-$T^{3'}$), 3.21 (m, 2H, $CCH_2$), 2.61 (m, 2H, $CNCH_2$), 2.29, 1.95 (m, 2H, HH'-2'-$T^{5'}$), 1.90 (s, 3H, $CH_3C$-5-$T^{5'}$), 1.88 (s, 3H, $CH_3C$-5-$T^{3'}$), 1.82, 1.40 (m, 2H, HH'-2'-$T^{3'}$), 1.06 (s, 9H, $SiC(CH_3)_3$-$T^{5'}$), 0.88 (s, 9H, $SiC(CH_3)_3$-$T^{3'}$), 0.063, 0.059 (d, 6H, $Si(CH_3)_2$). $^{13}C$ NMR (125.7 MHZ, $CDCl_3$): δ164.23, 164.09 (C-4-$T^{3'}$. C-4-$T^{5'}$), 150.70, 150.35 (C-2-$T^{3'}$, C-2-$T^{5'}$), 135.82, 135.65, 135.54, 134.65, 132.75, 132.51, 131.97, 130.12 (d), 128.32, 127.93, 127.89, 121.45, 119.76, 119.56, 115.63, 111.22 (d), 110.80, 101.26, 85.24 (d), 84.94, 84.76 (d), 84.44, 80.32, 74.02 (d), 72.55, 67.22 (d), 63.02, 39.89, 38.16, 33.18 (d), 26.67, 25.75, 23.45, 18.81, 18.12, 12.41 (d), −5.56, −5.62.

Example 9

Sp-(5'-O-tert-butyldimethylsilyl)thymid-3'-yl (3'-O-tert-butyl-diphenylsilyl)-thymid-5'-yl (S)-(1-cyano-3-indol-2-yl)isopropyl phosphorothioate Sp-8

To a solution of indole-oxazaphosphorine Sp-6eq/Rp-6ax (6:1) (307 mg, 0.526 mmol) in dry THF (10 mL) was added 3'-O-TBDPS-thymidine (253 mg, 0.526 mmol) followed by DBU (157 mL, 1.05 mmol). The reaction mixture was stirred at room temperature for 5 minutes and passed though a short silica gel column to filter off DBU. The column was eluted with $CH_3CN$. The solvent was evaporated to afford light yellow solid. This solid was redissolved in dry $CH_2Cl_2$ (5 mL), and Beaucage's reagent (150 mg, 0.75 mmol) was added. After 10 minutes, evaporation of the solvent followed by flash chromatography ($CH_2Cl_2$/$CH_3COCH_3$ 5:1) afforded 388.4 mg (68%) of the title compound as a light yellow solid.

M.p. 116–117° C. $^{31}P$ NMR (202.3 MHZ, $CDCl_3$): δ66.31 ppm. $^1H$ NMR (500 MHZ, $CDCl_3$): δ9.16, 9.13, 8.60 (3×s, 3H, NH-3-$T^{5'}$, NH-3-$T^{3'}$, NH-indole), 7.63–7.05 (m, 16H, aromatic H, H-6-$T^{3'}$, H-6-$T^{5'}$), 6.33 (s, 1H, H-3-indole), 6.27 (m, 1H, H-1'-$T^{5'}$), 6.17 (dd, 1H, $^3J$=9.0, 5.0 Hz, H-1'-$T^{3'}$), 4.91 (m, 2H, H-3'-$T^{3'}$, CHOP), 4.30 (m, 1H, H-3'-$T^{5'}$), 4.10 (m, 1H, H-4'-$T^{5'}$), 3.88 (m, 1H, H-4'-$T^{3'}$), 3.79 (m, 2H, H-4'-$T^{3'}$, H-5'-$T^{5'}$), 3.54, 3.45 (m, 2H, HH'-5'-$T^{3'}$), 3.19 (m, 2H, $CCH_2$), 2.65 (m, 2H, $CNCH_2$), 2.28 (m, 2H, H-2-$T^{3'}$, H-2'-$T^{5'}$), 2.01 (m, 1H, H'-2'-$T^{5'}$), 1.89 (s, 3H, $CH_3C$-5-$T^{5'}$), 1.86 (s, 3H, $CH_3C$-5-$T^{3'}$), 1.87 (m, 1H, H'-2'-$T^{3'}$), 1.06 (s, 9H, $SiC(CH_3)_3$-$T^{5'}$), 0.88 (s, 9H, $SiC(CH_3)_3$-$T^{3'}$), 0.068, 0.060 (d, 6H, $Si(CH_3)_2$). $^{13}C$ NMR (125.7 MHZ, $CDCl_3$): δ163.82, 163.17 (C-4-$T^{3'}$. C-4-$T^{5'}$), 150.35, 150.27(C-2-$T^{3'}$, C-2-$T^{5'}$), 136.33, 136.10, 135.79, 134.85, 132.96, 132.81, 131.61, 130.30, 128.33, 128.13, 128.06, 122.20, 120.24, 115.85, 111.36, 111.24, 110.94, 102.61, 86.32, 85.49, 85.40, 85.13, 85.01, 84.60, 80.75, 80.68, 77.29, 74.23, 74.15, 73.06, 67.86, 63.16, 39.92, 38.92 (d), 33.57 (d), 31.00, 26.90, 25.96, 23.96, 23.65, 19.06, 18.34, 12.58, 12.52, −5.33, −5.41. MS (FAB, NBA): 1097 (11.1%, M+H$^+$), 759 (5.4%), 377 (28.1%), 339 (51.7%), 182 (100%).

Example 10

Sp-(5'-O-tert-butyldimethylsilyl)thymid-3'-yl (3'-O-tert-butyl-diphenylsilyl)-thymid-5'-yl phosphorothioate Sp-9

To a solution of phosphorothioate triester Rp-7 (60 mg, 55.8 mmol) in methanol (1 mL) was added aqueous ammonia (20 mL, 28%). The solution was stirred at 50° C. for half an hour, neutralized with HCl (6N) and extracted with ethyl acetate (3×10 mL). The combined extracts were dried over anhydrous sodium sulfate. The solvent was evaporated and the residue was purified by flash chromatography (acetone/triethylamine 10:1) to give 32 mg (58%) of the title compound as a white solid which is the triethylammonium salt.

M.p. 97–98° C. $^{31}P$ NMR (202.3 MHZ, $CD_3OD$): δ58.96 ppm. $^1H$ NMR (500 MHZ, $CDCl_3$): δ7.76 (d, 1H, J=1.0 Hz, H-6-$T^{5'}$), 7.56, 7.31 (m, 10H, $C_6H_5SiC_6H_5$), 7.48 (d, 1H, J=1.0 Hz, H-6-$T^{3'}$), 6.39 (dd, 1H, J=9.2, 5.0 Hz, H-1'-$T^{5'}$), 6.05 (dd, 1H, J=8.8, 5.0 Hz, H-1'-$T^{3'}$), 4.88 (m, 1H, H-3'-$T^{3'}$), 4.47 (m, 1H, H-3'-$T^{5'}$), 3.98 (m, 1H, H-4'-$T^{3'}$), 3.95 (m, 1H, H-4'-$T^{5'}$), 3.74, 3.50 (m, 2H, HH'-5'-$T^{3'}$), 3.67 (m, 2H, HH'-5'-$T^{5'}$), 2.86, 1.10 (q, t, N($CH_2CH_3$)$_3$), 2.28 (m, 1H, H-2'-$T^{3'}$), 2.00 (m, 3H, H'-2'-$T^{3'}$, HH'-2'-$T^{5'}$), 1.83 (d, 3H, J=1.0 Hz, $CH_3C$-5-$T^{5'}$), 1.76 (d, 3H, J=1,0 Hz, $CH_3C$-5-$T^{3'}$), 0.98 (s, 9H, $SiC(CH_3)_3$-$T^{5'}$), 0.80 (s, 9H, $SiC(CH_3)_3$-$T^{3'}$), 0.009, 0.003 (d, 6H, Si(CH$_3$)$_2$). $^{13}$C NMR (125.7 MHZ, CD$_3$OD): δ166.38, 166.28 (C-4-T$^{3'}$. C-4-T$^{5'}$), 152.48, 151.95 (C-2-T$^{3'}$, C-2-T$^{5'}$), 138.04, 137.26, 136.82, 136.80, 134.35, 134.25, 131.18, 131.08, 129.02, 128.94, 112.22, 111.09, 88.03, 87.95, 87.61 (d), 86.34, 86.16, 77.98 (d), 76.30, 66.46 (d), 64.81, 41.36, 40.58 (d), 27.29, 26.41, 19.68, 19.16, 12.60 (d), −5.22, −5.28. MS (FAB, NBA): 937 (M+Na$^+$).

Example 11

Rp-(5'-O-tert-butyldimethylsilyl)thymid-3'-yl (3'-O-tert-butyl-diphenylsilyl)-thymid-5'-yl phosphorothioate Rp-10

Using the same procedure as illustrated above in Example 10, a solution of phosphorothioate triester Sp-8 (0.2248 g, 0.205 mmol) in aqueous ammonia (20 mL, 28%) was stirred at 50° C. for half an hour. After purification by flash chromatography (acetone/triethylamine 10:1), 0.2 g (quantitative yield) of the title compound was obtained as a white solid.

$^{31}$P NMR (202.3 MHZ, CD$_3$OD): δ59.07 ppm. $^1$H NMR (500 MHZ, CD$_3$OD): δ7.69 (d, 1H, J=1.0 Hz, H-6-T$^{5'}$), 7.49, 7.24 (m, 10H, C$_6$H$_5$SiC$_6$H$_5$), 7.44 (d, 1H, J=1.0 Hz, H-6-T$^{3'}$), 6.32 (dd, 1H, J=9.0, 5.5 Hz, H-1'-T$^{5'}$), 6.02 (dd, 1H, $^3$J=8.5, 5.5 Hz, H-1'-T$^{3'}$), 4.83 (m, 1H, H-3'-T$^{3'}$), 4.40 (m, 1H, H-3'-T$^{5'}$), 4.05 (m, 1H, H-4'-T$^{3'}$), 3.92 (m, 1H, H-4'-T$^{5'}$), 3.72 (m, 2H, H-5'-T$^{3'}$, H-5'-T$^{5'}$), 3.45 (m, 1H, H'-5'-T$^{5'}$), 2.84, 1.04 (q, t, N(CH$_2$CH$_3$)$_3$), 2.07 (m, 2H, H-2'-T$^{3'}$, H-2'-T$^{5'}$), 1.92 (m, 1H, H'-2'-T$^{5'}$), 1.80 (m, 1H, H'-2'-T$^{3'}$), 1.76 (br, H$_2$O, CH$_3$C-5-T$^{5'}$), 1.71 (d, 3H, J=1,0 Hz, CH$_3$C-5-T$^{3'}$), 0.91 (s, 9H, SiC(CH$_3$)$_3$-T$^{5'}$), 0.75 (s, 9H, SiC(CH$_3$)$_3$-T$^{3'}$), −0.041, −0.047 (d, 6H, Si(CH$_3$)$_2$). $^{13}$C NMR (125.7 MHZ, CD$_3$OD): δ166.36, 166.21 (C-4-T$^{3'}$. C-4-T$^{5'}$), 152.44, 151.96 (C-2-T$^{3'}$, C-2-T$^{5'}$), 138.03, 137.11, 136.86, 136.81, 134.36, 134.26, 131.19, 131.13, 129.07, 129.00, 112.13, 111.26, 88.11, 88.06, 88.04, 88.03, 86.29, 88.24, 78.53, 78.50, 76.20, 66.47, 66.43, 64.90, 47.45, 41.57, 40.43, 40.39, 27.39, 26.51, 22.08, 19.74, 19.04, 12.72, 12.67, 9.68, −5.08, −5.16.

Example 12

Sp-Tetrabutylammonium thymid-3'-yl thymid-5'-yl phosphorothioate Sp-11

A solution of TBAF (1.0 M in DMF, 4 mL) containing dimer Sp-9 (20 mg, 17.5 mmol) was stirred at room temperature for one hour. The solvent was evaporated under vacuum and the residue was purified by flash chromatography (acetone/triethylamine 1:1) to give 15 mg (95%)of the title compound as a sticky solid dimer as the tetrabutylammonium salt.

$^{31}$P NMR (202.3 MHZ): δ58.96 ppm (CD$_3$OD), 55.45 ppm (D$_2$O). $^1$H NMR (500 MHZ, CD$_3$OD): δ7.80 (d, 1H, J=1.0 Hz, H-6-T$^{5'}$), 7.78 (d, 1H, J=1.5 Hz, H-6-T$^{3'}$), 6.29 (dd, 1H, J=8.0, 6.0 Hz, H-1'-T$^{5'}$), 6.22 (dd, 1H, J=8.0, 6.0 Hz, H-1'-T$^{3'}$), 4.98 (m, 1H, H-3'-T$^{3'}$), 4.45 (m, 1H, H-3'-T$^{5'}$), 4.12 (m, 1H, H-4'-T$^{3'}$), 4.09, 3.98 (m, 2H, HH'-5'-T$^{5'}$), 3.98 (m, 1H, H-4'-T$^{5'}$), 3.74 (m, 2H, HH'-5'-T$^{3'}$), 3.17, 1.59, 1.35, 0.94 (N(CH$_2$CH$_2$CH$_2$CH$_3$)$_4$), 2.40 (m, 1H, H-2'-T$^{3'}$), 2.20 (m, 2H, H'-2'-T$^{3'}$, H-2'-T$^{5'}$), 2.12 (m, 1H, H'-2'-T$^{5'}$), 1.89 (d, 3H, J=1.0 Hz, CH$_3$C-5-T$^{5'}$), 1.80 (d, 3H, J=1,0 Hz, CH$_3$C-5-T$^{3'}$). $^{13}$C NMR (125.7 MHZ, CD$_3$OD): δ166.45, 166.34 (C-4-T$^{3'}$. C-4-T$^{5'}$), 152.40, 152.24 (C-2-T$^{3'}$, C-2-T$^{5'}$), 138.08, 138.06, 112.02, 111.53, 87.61 (d), 87.31 (d), 86.16 (d), 77.06 (d), 72.87, 66.69 (d),62.79, 59.39 (t), 40.79, 40.01 (d), 24.69, 20.61, 13.85, 12.60, 12.37.

Example 13

Rp-Tetrabutylammonium thymid-3'-yl thymid-5'-yl phosphorothioate Rp-12

Using the procedures illustrated in Example 12 above Compound Rp-10 (80.4 mg, 0.079 mmol) was desilylated with TBAF to give 50 mg (78%) of the title compound as a sticky solid.

Two diastereomers Rp-12 and Sp-12 were observed using $^{31}$P NMR in a ratio of 21:1. $^{31}$P NMR (202.3 MHZ, CD$_3$OD): δ Rp-12, 58.92 ppm (95.4%), Sp-12, 58.99 ppm (4.6%).

$^1$H NMR (500 MHZ, CD$_3$OD): δ7.85 (d, 1H, J=1.0 Hz, H-6-T$^{5'}$), 7.80 (d, 1H, J=1.0 Hz, H-6-T$^{3'}$), 6.29 (dd, 1H, J=8.0, 6.0 Hz, H-1'-T$^{5'}$), 6.22 (dd, 1H, $^3$J=8.2, 5.5 Hz, H-1'-T$^{3'}$), 5.00 (m, 1H, H-3'-T$^{3'}$), 4.45 (m, 1H, H-3'-T$^{5'}$), 4.15 (m, 1H, H-4'-T$^{3'}$), 4.06 (m, 2H, HH'-5'-T$^{3'}$), 3.98 (m, 1H, H-4'-T$^{5'}$), 3.77 (m, 2H, HH'-5'-T$^{5'}$), 3.17, 1.59, 1.35, 0.95 (N(CH$_2$CH$_2$CH$_2$CH$_3$)$_4$), 2.40 (m, 1H, H-2'-T$^{5'}$), 2.20 (m, 2H, H-2'-T$^{3'}$, H'-2'-T$^{5'}$), 2.14 (m, 1H, H'-2'-T$^{3'}$), 1.91 (d, 3H, J=1.o Hz, CH$_3$C-5-T$^{5'}$), 1.81 (d, 3H, J=1,0 Hz, CH$_3$C-5-T$^{3'}$). $^{13}$C NMR (125.7 MHZ, CD$_3$OD): δ166.43, 166.28 (C-4-T$^{3'}$. C-4-T$^{5'}$), 152.39, 152.21 (C-2-T$^{3'}$, C-2-T$^{5'}$), 138.12, 138.03, 112.00, 111.48, 87.85, 87.80, 87.49, 87.42, 86.20, 86.08, 77.49, 77.45, 72.94, 66.35, 66.30, 62.83, 59.44, 59.42, 59.39, 40.87, 39.88, 39.84, 24.70, 20.62, 13.87, 12.61, 12.40.

Example 14

Attachment of 5'-O-DMT-thymidine to CPG

To a dry 6 mL-hypovial was added 5'-O-DMT-thymidine (109 mg, 0.2 mmol), CPG with sarcosinyl-succinonyl linker (1.0 g), 4-DMAP (12 mg, 0.1 mmol), triethylamine (80 mL), 1-(3-dimethylaminopropyl)-3-ethylcarbodiimide hydrochloride (DEC) (384 mg, 2.0 mmol) and anhydrous pyridine (5 mL). The mixture was shaken at room temperature for 24 hours. Pentachlorophenol (134 mg, 0.5 mmol) was added, and the mixture was shaken for an additional period of 16 hours. The CPG was filtered off and washed successively with pyridine, CH$_2$Cl$_2$, and ether. The CPG was treated with reagent grade piperidine (5 mL), and the slurry was shaken for 10 minutes. The resulting CPG was filtered off, washed successively with CH$_2$Cl$_2$ and ether, and dried under vacuum.

The dry CPG was capped by mixing it with equal parts of a solution of 0.5 M acetic anhydride in THF and a solution of 0.5 M 4-DMAP/2,4,6-trimethylpyridine in THF (4 mL each). The slurry was shaken for 2 hours followed by washing successively with pyridine, CH$_2$Cl$_2$, THF and ether. Drying under vacuum afforded the immobilized thymidine (0.89 g).

The loading amount was measured by trityl analysis. The CPG-thymidine (6.0 mg) was treated with 5% trichloroacetic acid in 1,2-dichloroethane (10 mL). The UV absorbance of the solution was 1.7283 at 504 nm. The loading amount was therefore 37.9 mmol/g according to the calculation (A·V·10$^3$)/(76 W). (A: the UV absorbance at 504 nm; V: volume of the solution; W: the weight of CPG.)

The solid support bound thymidine (0.5 g) was placed in a sintered glass funnel and washed with 3% trichloroacetic acid until no red color was observed. The resulting thymidine attached to CPG having a free 5'-OH group was dried under vacuum.

Example 15

Sp-Indole-oxazaphosphorine Sp-13

Using the procedures illustrated in Example 6 above (S)-4 (3.0 g, 15 mmol), from Example 5 above, was treated with PCl₃ (1.3 mL, 15 mmol) and 5'-O-DMT-thymidine (8.2 g, 15 mmol) to give 5.43 g (47%) of the title compound as a light yellow solid.

M.p. 112–113° C. Two diastereoisomers of the title compound were obtained in a ratio of 13:1 as established by $^{31}$P NMR. $^{31}$P NMR (202.3 MHZ, CDCl₃): δ121.58 ppm (93%), 122.17 ppm (7.0%).

$^1$H NMR (500 MHZ, CDCl₃): δ8.93 (br s, 1H, NH), 7.55 (s, 1H, H-6), 7.24, 6.83 (m, 17H, aromatic H), 6.40 (m, 2H, H-3-indole, H-1'), 4.95 (m, 1H, H-3'), 4.41 (m, 1H, CHOP), 4.04 (m, 1H, H-4'), 3.80 (d, 6H, 2×OCH₃), 3.50, 3.31 (m, 2H, HH'-5'), 3.10 (m, 2H, CH₂-Indole), 2.72 (m, 2H, CH₂CN), 2.49, 2.24 (m, 2H, HH'-2'), 1.41 (s, 3H, CH₃C-5). $^{13}$C NMR (125.7 MHZ, CDCl₃): δ163.44 (C-4), 158.62 (C-2), 150.20, 143.92, 137.74, 137.61, 135.22, 134.98, 134.93, 133.58, 129.96, 128.00, 127.85, 127.09, 122.55, 121.63, 120.44, 115.76, 113.13 (d), 111.33, 110.30 (d), 104.17, 86.89, 85.18 (d), 84.49, 75.07 (d), 70.20 (d), 62.75, 55.15, 39.45 (d), 30.75 (d), 29.52, 25.14 (d), 11.56. MS (FAB, NBA): 795 (M+Na⁺, 4.6%), 773 (M+H⁺, 1.0%), 772 (1.8%).

Example 16
Preparation of Dimer Having Alkylphosphonate Internucleotide Linkage 14

To the sintered glass funnel was added solid support bound thymidine (27 mg, 1 μmol) as prepared in Example 14 above and a solution of Sp-13 in CH₃CN (0.2 mL, 0.1 M) form Example 15 above. DBU (30 μL, 0.2 mmol) was added via syringe. After five minutes the solid support was washed with CH₃CN (3×2 mL) and treated with Beaucage reagent (0.1 mL, 0.1 M in THF). After detritylation with 3% trichloroacetic acid in 1,2-dichloroethane, the solid support was cleaved with NH₄OH (28%) at 50° C. for two hours. The solution was evaporated to dryness with a phase-drier, the residue was dissolved in HPLC-grade water (1 mL) and filtered to give a solution of the title compound.

MS (FAB) m/z: 735 (M+Na⁺, 4.52%), 713 (M+H⁺, 100.0%), 714 (42.95%), 715 (9.40%).

Example 17
5'-O-DMT-3'-O-TBDPS-[2-cyano-1-(2-methylene-indole)-ethylphosphonate] TT dimer 15

To a solution of Sp-13/Rp-13 (12:1) (200 mg, 0.26 mmol) in dry THF (10 mL) was added 5 equivalents of DBU (194 μL). After 5 minutes, 1 eq. of 3'-O-TBDPS-thymidine (124 mg) was added. The mixture was stirred for 5 minutes. The solvent was evaporated, and the crude product was purified by flash chromatography (EtOAc) to give 140 mg (43%) of the title compound as a light yellow solid (m.p. 127–128° C.).

The title compound gave four peaks using $^{31}$P NMR. $^{31}$P NMR (202.3 MHZ, CDCl₃): δ29.88 ppm (14.2%), 29.66 ppm (1.7%), 28.97 ppm (21.0%), 28.79 ppm (63.1%).

$^1$H NMR (500 MHZ, CDCl₃): δ9.52 (s, 1H, NH-3-T$^{5'}$), 9.44 (s, 1H, NH-3-T$^{3'}$), 9.10 (s, 1H, NH), 7.62–6.77 (m, 27H, aromatic H), 7.48 (s, 1H, H-6-T$^{5'}$), 7.13 (s, 1H, H-6-T$^{3'}$), 6.30 (m, 2H, H-1'-T$^{3'}$, NCCH), 6.13 (m, 1H, H-1'-T$^{5'}$), 5.16 (m, 1H, H-3'-T$^{3'}$), 4.29 (m, 1H, H-3'-T$^{5'}$), 4.10 (m, 1H, H-4'-T$^{5'}$), 4.06 (m, 1H, H-4'-T$^{3'}$), 3.88, 3.82 (m, 2H, HH'-5'-T$^{3'}$), 3.73, 3.72 (d, 6H, 2×CH₃O), 3.43, 3.28 (m, 2H, HH'-5'-T$^{5'}$), 3.17 (m, 2H, CCH₂), 2.90 (m, 1H, PCH), 2.50 (m, 1H, H-2'-T$^{3'}$), 2.36 (m, 3H, H'-2'-T$^{3'}$, CNCH₂), 2.24, 2.06 (m, HH'-2'-T$^{5'}$), 1.77 (s, 3H, CH₃C-5-T$^{5'}$), 1.43 (s, 3H, CH₃C-5-T$^{3'}$), 1.06 (s, 9H, SiC(CH₃)₃). HRMS (FAB, M+H⁺): C₆₉H₇₄N₆O₁₃PSi, Calcd. 1253.482079, Found 1253.482500.

Example 18
5'-O-DMT-3'-O-TBDMS-cyanoethylphosphonate T-T dimer 16

5'-O-DMT-thymidine cyanoethoxydiisopropylamino-phosphoramidite was reacted with 3'-O-TBDMS-thymidine following standard solution phase phosphoramidite methods to give 5'-O-DMT-3'-O-TBDMS-cyanoethoxyphosphite T-T dimer. The cyanoethoxyphosphite dimer was purified by silica gel flash column chromatography using hexane: ethyl acetate (3/7, v/v) as the eluent to give several fractions. The purest fraction was shown to contain a mixture of diastereomers at a ration of 1:10 with the diastereomer of lower concentration eluting faster than the major diastereomer. $^{31}$P NMR analysis of the mixture shows two peaks for the mixture of diastereomers ($^{31}$P NMR: 140.0 ppm for the fast eluted, 139.8 ppm for the slow eluted). This mixture was dissolved in CH₂Cl₂ followed by treatment with DBU (10 eq.) at room temperature. The reaction was complete in 10 hours giving the title alkylphosphonate as a mixture of diastereomers in a ratio of 1:10 ($^{31}$P NMR: 28.4 ppm for the fast eluted, 27.6 ppm for the slow eluted).

Example 19
Preparation of Thymidine 12mer having a Cyanoethyl Alkylphosphonate Internucleoside Linkage at the 3' Terminus Commercially available 5'-O-DMT-2-cyanoethyl-N,N-diisopropylamino thymidine phosphoramidite (0.1 M in CH₃CN) is coupled to commercially available thymidine CPG (1 mmol) using standard phosphoramidite coupling protocols to give the 5'-O-DMT-2-cyanoethyl protected phosphite dimer attached to solid support at the 3'-O-position. The automated synthesis column where the first coupling is performed is extensively washed with CH₃CN, and a mixture of acrylonitrile (0.1 M) and DBU (0.5 M) in dry CH₃CN is delivered to the washed dimer for 1 minute. After 15 minutes contact time, the solid support is washed with CH₃CN. A total of 10 additional coupling cycles are carried out using 5'-O-DMT-2-cyanoethyl-N,N-diisopropylamino thymidine phosphoramidite at each coupling following standard phosphoramidite protocols to give a 12mer. The T-12mer is removed from the solid support by treatment with concentrated aqueous ammonia for 2 hours at room temperature. The resulting solution is evaporated. The product is isolated by reversed phase HPLC on a DeltaPak column (C18, 15 mm, 3.9×300 mm). A linear gradient is used for the separation (from 0 to 60% buffer B in buffer A, in 40 minutes at a flow rate of 1.5 mL min$^{31}$ $^1$., buffer A=0.1 M ammonium acetate, buffer B=80% aq CH₃CN). The collected fractions are evaporated, the product is desalted and characterized by capillary gel electrophoresis and ESMS.

Example 20
Preparation of Thymidine 12mer having a Cyanoethyl Alkylphosphonate Internucleoside Linkage at the 3' Terminus Thymidine 5'-O-DMT-3'-H-phosphonate (triethylammonium salt, 0.1 M in pyridine) is coupled to commercially available thymidine CPG (1 mmol) on an automated synthesizer reaction column using the standard coupling protocol. Pivaloyl chloride is used as an activator to give 5'-O-DMT-thymidine dimer having an H-phosphonate internucleoside linkage attached to a solid support at the 3'-O-position. The dimer is thoroughly washed with CH₃CN, and treated with N,O-bis(trimethylsilyl) trifluoroacetamide (0.1 M in CH₃CN) for 3 min followed by treatment with a mixture of acrylonitrile (0.1 M) and DBU (0.5 M) in dry CH₃CN (1 minute). After 15 minutes contact time, the solid support bound dimer is washed with CH₃CN. A total of 10 additional coupling cycles are carried out using 5'-O-DMT-2-cyanoethyl-N,N-diisopropylamino thymidine phosphoramidite (0.1 M in CH₃CN) at each coupling following standard phosphoramidite protocols using 1H-tetrazole as an activator to give a 12mer. The resulting 12mer is removed from the solid support by treatment with concentrated aqueous ammonia for 2 hours at room temperature. The solution is evaporated and the product is isolated by reversed phase HPLC as described as per the procedure illustrated in Example 19 above. The product containing fractions are evaporated and the product is desalted and characterized by capillary gel electrophoresis and ESMS.

Example 21

Preparation of Thymidine 12mer having a Cyanoethyl Alkylphosphonate Internucleoside Linkage at the 5' Terminus Commercially available 5'-O-DMT-2-cyanoethyl-N,N-diisopropylamino thymidine phosphoramidite (0.1 M in CH₃CN) is coupled to commercially available thymidine CPG (1 mmol) using standard phosphoramidite coupling protocols to give the 5'-O-DMT-2-cyanoethyl protected phosphite dimer attached to solid support at the 3'-O-position. A total of 10 additional coupling cycles are carried out using 5'-O-DMT-2-cyanoethyl-N,N-diisopropylamino thymidine phosphoramidite at each coupling following standard phosphoramidite protocols to give the phosphotriester 11mer. The 5'-terminal DMT group is removed and the solid support-bound 11mer is treated with a further 5'-O-DMT-2-cyanoethyl-N,N-diisopropylamino thymidine phosphoramidite (0.1 M in CH₃CN) in the presence of 1H-tetrazole. The solid support is thoroughly washed with CH₃CN, and further treated with a mixture of acrylonitrile (0.1 M) and DBU (0.5 M) in dry CH₃CN for 1 minute. After 15 minutes contact time, the solid support is washed with CH₃CN. The solid support is treated with concentrated aqueous ammonia for 2 hours at room temperature and evaporated. The product is isolated by reversed phase HPLC as illustrated in Example 19 above. The product containing fractions are evaporated and the product is desalted and characterized by capillary gel electrophoresis and ESMS.

Example 22

5'-O-DMT-3'-O-TBDMS-3-trifluoroacetylyamino-propylphosphonate TT dimer

5'-O-DMT-3'-O-TBDMS-cyanoethylphosphonate T-T dimer (16, Example 18) is dissolved in a suitable solvent and treated with BH₃.SMe₂ complex. The resulting 3-aminopropylphosphonate is protected by treatment with CF₃COOEt to give the title compound.

Example 23

Preparation of 5'-O-DMT-3'-O-[2-cyanoethyl-N,N-diisopropyl]phosphoramidite cyanoethyl alkylphosphonate TT dimer 5'-O-DMT-3'-O-TBDMS-cyanoethylphosphonate T-T dimer (16, Example 18) is dissolved in a suitable solvent and treated with Et₃N-3HF (triethylamine trihydrofluoride) complex to give the free 3'-OH at the 3'-end of the dimer. The dimer is further treated with 2-cyanoethyl diisopropylchlorophosphoramidite to form the phosphoramidite TT dimer.

Example 24

5'-O-DMT-3'-O-[2-cyanoethyl-N,N-diisopropyl]phosphoramidite-3-trifluoroacetylyamino-propylphosphonate TT dimer 5'-O-DMT-3'-O-TDMS-3-trifluoroacetylyamino-propylphosphonate TT dimer (Example 22) is dissolved in a suitable solvent and treated with Et₃N-3HF (triethylamine trihydrofluoride) complex to give the free 3'-OH at the 3'-end of the dimer. The dimer is further treated with 2-cyanoethyl diisopropylchlorophosphoramidite to form the phosphoramidite TT dimer.

Example 25

5'-O-DMT-3'-O-TBDMS-3'-cholesteryl-oxy-carbonyl-aminopropyl phosphonate TT dimer The 5'-O-DMT-3'-O-TBDMS-3-aminopropylphosphonate TT dimer of Example 22 above is treated with cholesteryl chloroformate in pyridine/CH₂Cl₂ (50:50 v/v) to give the title compound.

Example 26

5'-O-DMT-3'-O-TBDMS-3'-cholesteryl-oxy-carbonyl-aminopropyl phosphonate TT dimer 5'-O-DMT-3'-O-TBDMS-3'-cholesteryl-oxy-carbonyl-aminopropyl phosphonate TT dimer (Example 25) is dissolved in a suitable solvent and treated with Et₃N-3HF to deblock the 3'-hydroxyl group. The dimer is further treated with 2-cyanoethyl diisopropyl-chlorophosphoramidite to form the cholesteryl conjugated phosphoramidite TT dimer.

Example 27

Preparation of a 9mer Alkylphosphonate Gapmer $T_aT_aT$ TTT $T_aT_aT$ ($T_a$=3-dimethylaminopropylalkylphosphonate internucleoside linkage)

Commercially available 5'-O-DMT-2-cyanoethyl-N,N-diisopropylamino thymidine phosphoramidite (0.1 M in CH₃CN) is coupled to commercially available thymidine CPG (1 mmol) using standard phosphoramidite coupling protocols on an automated synthesizer to give the 5'-O-DMT-2-cyanoethyl protected phosphite dimer attached to solid support at the 3'-O-position. The automated synthesis column containing the solid support bound dimer is extensively washed with CH₃CN, and a mixture of acrylonitrile (0.1 M) and DBU (0.5 M) in dry CH₃CN is delivered to the washed dimer for 1 minute. After 15 minutes contact time, the solid support is washed with CH₃CN.

The resulting cyanoethyl alkylphosphonate dimer is treated with BH₃.SMe₂ complex in CH₃CN and washed with acetonitrile. The resulting 3-aminopropylphosphonate is further treated with methyliodide to form the 5'-O-DMT-3-dimethylaminopropylphosphonate $T_aT$ dimer attached to solid support at the 3'-terminus.

The dimer is extended by treatment with TCA to remove the 5'-O-DMT group and further treatment with a 5'-O-DMT-2-cyanoethyl-N,N-diisopropylamino thymidine phosphoramidite following standard phosphoramidite protocols. The resulting phosphite triester internucleoside linkage is treated as illustrated above to form the 5'-O-DMT-3-dimethylaminopropylphosphonate $T_aT_aT$ trimer attached to solid support at the 3'-terminus.

Alternatively the $T_aT_aT$ trimer can be prepared as per the procedure of Example 20. The dimer is prepared, reduced and functionalized with methyliodide to give the $T_aT$ dimer. The dimer is extended by treatment with TCA to remove the 5'-O-DMT group and coupling a further H-phosphonate T nucleoside using a hindered acyl halide activating group (pivaloyl chloride for example) following standard H-phosphonate coupling protocols. The resulting trimer is treated as previously stated to give the $T_aT_aT$ trimer attached to solid support at the 3'-terminus.

The $T_aT_aT$ trimer is extended by 4 additional coupling cycles using 5'-O-DMT-2-cyanoethyl-N,N- diisopropylamino thymidine phosphoramidite at each coupling following standard phosphoramidite protocols to give the phosphotriester 7mer $T_aT_aT$ TTT T with phosphodiester internucleotide linkages (alternatively oxidation can be performed to give the P=S linkages).

The 7mer is further treated as illustrated above with T phosphoramidites followed by treatment with DBU and reduction to give the title gapmer attached to solid support. The title gapmer can be removed from the solid support via treatment with aqueous concentrated ammonia. Removal of the 5'-O-DMT group will give the title gapmer.

Example 28

Preparation of a Substantially Diastereomerically Pure 6mer Alkylphosphonate $T_aT_aT_aT_aT_aT$ ($T_a$=3-trifluoroacetylaminopropylalkylphosphonate internucleoside linkage)

To a solution of Sp-13 (200 mg, 0.26 mmol), purified by HPLC, in dry THF (10 mL) is added 5 equivalents of DBU (194 µL). After 5 minutes, 1 eq. of 3'-O-TBDPS-thymidine (124 mg) is added. The mixture is stirred for 5 minutes. The solvent is evaporated, and the crude product is purified by flash chromatography (EtOAc) to give 5'-O-DMT-3'-O-TBDPS-[2-cyano-1-(2-methylene-indole)-ethylphosphonate] TT dimer as essentially a pure diastereomer. The alkylphosphonate compound is treated with a reducing agent to reduce the cyano group. The resulting amino group is treated with $CF_3COOEt$ to give the trifluoroacetyl protected amino group. The 5'-O-DMT group is removed using TCA and the reaction sequence illustrated above is repeated to give the trimer having essentially diastereomerically pure internucleoside linkages. Repetition of the procedure 3 additional times will form the hexamer having essentially diastereomerically pure internucleoside linkages.

Example 29

Preparation of a Substantially Diastereomerically Pure 6mer Alkylphosphonate $T_aT_aT_aT_aT_aT$ ($T_a$=3-(cholesteryloxycarbonyl)aminopropylalkylphosphonate internucleoside linkage)

To a solution of Sp-13 (200 mg, 0.26 mmol), purified by HPLC, in dry THF (10 mL) is added 5 equivalents of DBU (194 µL). After 5 minutes, 1 eq. of 3'-O-TBDPS-thymidine (124 mg) is added. The mixture is stirred for 5 minutes. The solvent is evaporated, and the crude product is purified by flash chromatography (EtOAc) to give 5'-O-DMT-3'-O-TBDPS-[2-cyano-1-(2-methylene-indole)-ethylphosphonate] TT dimer as essentially a pure diastereomer. The alkylphosphonate compound is treated with a reducing agent to reduce the cyano group. The resulting amino group is treated with cholesterol chloroformate in pyridine/methylene chloride to give the cholesterol derivatized amino group. The 5'-O-DMT group is removed using TCA and the reaction sequence illustrated above is repeated to give the trimer having essentially diastereomerically pure internucleoside linkages. Repetition of the procedure 3 additional times will form the hexamer having essentially diastereomerically pure internucleoside linkages.

What is claimed is:

1. A process of preparing an alkylphosphonate compound of the structure:

wherein
each $M_1$ and $M_2$ independently, are hydrogen or a hydroxyl protecting group or one of $M_1$ and $M_2$ is hydrogen or a hydroxyl protecting group and the other of $M_1$ and $M_2$ is a covalent attachment to a solid support;
each J is, independently, hydrogen, a 2'-substituent group, or a protected 2'-substituent group;
$R_1$ is an electron withdrawing group;
$X_2$ is hydrogen or $-(CH_2)_m-E_2$;
$E_2$ is hydrogen, alkyl, aryl, aralkyl, substituted aryl, a heterocycle, mixed heterocycle or heteroaryl;
m is 0, 1, 2 or 3; and
Bx is a heterocyclic base moiety;
comprising the steps of:
a) selecting a dimeric trialkylphosphite compound of the structure:

and
b) treating said dimeric trialkylphosphite compound, in a solvent, with a base under conditions of time temperature and pressure to form said alkylphosphonate compound.

2. The process of claim 1 wherein one of $M_1$ and $M_2$ is a hydroxyl protecting group and the other of $M_1$ and $M_2$ is a covalent attachment to a solid support.

3. The process of claim 1 wherein both of $M_1$ and $M_2$ are hydroxyl protecting groups.

4. The process of claim 1 wherein said electron withdrawing group is CN, $COOR_5$ wherein $R_5$ is $C_1-C_8$ alkyl, $NO_2$, $CF_3$, aryl, halogen or substituted aryl wherein said substituents are halogen, cyano, $C_1$–$C_6$ alkyl, perhalo $C_1$–$C_3$, alkyl, alkoxy, nitro, nitroso or carboxylate.

5. The process of claim 4 wherein said electron withdrawing group is CN or $NO_2$.

6. The process of claim 1 wherein $X_2$ is H and $R_1$ is CN.

7. The process of claim 1 wherein said alkylphosphonate compound is prepared as substantially a single diastereomer.

8. The process of claim 1 wherein said dimeric trialkylphosphite compound is substantially diastereomerically pure.

9. The process of claim 1 wherein said base is 1,8-diazabicyclo[5.40]undec-7-ene (DBU), diisopropylethylamine (Hunig's base), a secondary amine, piperidine, morpholine, or piperazine.

10. The process of claim 1 wherein said solvent is DMF, DMSO, THF, THP or $CH_3CN$.

11. The process of claim 1 further comprising:

treating said alkylphosphonate compound with a chemical compound under conditions of time, temperature and pressure effective to reduce or modify said electron withdrawing group and optionally treating said alkylphosphonate compound having said reduced or modified electron withdrawing group with a chemical functional group having a reactive moiety thereon, to form an alkylphosphonate compound of the structure:

wherein each $M_1$ and $M_2$ independently, are hydrogen or a hydroxyl protecting group or one of $M_1$ and $M_2$ is hydrogen or a hydroxyl protecting group and the other of $M_1$ and $M_2$ is a covalent attachment to a solid support;

each J is, independently, hydrogen, a 2'-substituent group or a protected 2'-substituent group;

$R_2$ is a group having the formula —$(CH_2)_m N(R_3)(R_4)$, —$N(R_3)(R_4)$, or —$C(O)N(R_3)(R_4)$;

each $R_3$ and $R_4$ independently, are H, $C_1$–$C_{10}$ alkyl, $C_1$–$C_{10}$ alkylamino, $C_1$–$C_{10}$ alkyl substituted alkylamino or a nitrogen protecting group;

each $X_2$ is hydrogen or —$(CH_2)_m$—$E_2$;

$E_2$ is hydrogen, alkyl, aryl, aralkyl, substituted aryl, a heterocycle, mixed heterocycle or heteroaryl;

each m is, independently, 0, 1, 2 or 3; and

Bx is a heterocyclic base moiety.

12. The process of claim 11 wherein said chemical compound is a reducing agent.

13. The process of claim 12 wherein said reducing agent is $BH_3.SMe_2$, $NaBH_4$ and $CoCl_2.6H_2O$, or $LiBH_4$/MeOH and diglyme.

14. The process of claim 11 wherein $X_2$ is H and $R_2$ is —$CH_2N(H)(R_3)$ where $R_3$ is $C_1$–$C_{10}$ alkyl.

15. The process of claim 11 wherein said chemical compound is ammonia, a primary amine or a secondary amine wherein the substituents are $C_1$–$C_{10}$ alkyl.

16. The process of claim 15 wherein said chemical compound is ammonia, methylamine, dimethylamine, or dimethylaminoethlyamine.

* * * * *